US 8,357,704 B2

(12) United States Patent
Johnson et al.

(10) Patent No.: US 8,357,704 B2
(45) Date of Patent: Jan. 22, 2013

(54) FUSED HETEROCYCLIC COMPOUNDS AS INHIBITORS OF POTASSIUM CHANNEL FUNCTION

(75) Inventors: James A. Johnson, Pennington, NJ (US); John Lloyd, Yardley, PA (US); Alexander Kover, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 111 days.

(21) Appl. No.: 12/797,915

(22) Filed: Jun. 10, 2010

(65) Prior Publication Data

US 2010/0247534 A1    Sep. 30, 2010

Related U.S. Application Data

(62) Division of application No. 11/104,856, filed on Apr. 13, 2005, now Pat. No. 7,772,232.

(60) Provisional application No. 60/563,143, filed on Apr. 15, 2004.

(51) Int. Cl.
C07D 231/56     (2006.01)
C07D 261/20     (2006.01)
C07D 277/82     (2006.01)
C07D 285/14     (2006.01)
C07D 209/86     (2006.01)
A61K 31/416     (2006.01)
A61K 31/423     (2006.01)
A61K 31/426     (2006.01)
A61K 31/41      (2006.01)
A61K 31/403     (2006.01)
A61P 9/06       (2006.01)

(52) U.S. Cl. ........ 514/361; 514/406; 514/378; 514/367; 514/411; 548/360.1; 548/241; 548/164; 548/126; 548/444

(58) Field of Classification Search .................. 548/241, 548/360.1, 164, 126, 444; 514/379, 406, 514/378, 367, 381, 411
See application file for complete search history.

(56) References Cited

U.S. PATENT DOCUMENTS

| | | |
|---|---|---|
| 3,097,209 A | 7/1963 | Janssen |
| 3,978,044 A | 8/1976 | Vincent et al. |
| 4,298,734 A | 11/1981 | Temple, Jr. |
| 4,472,398 A | 9/1984 | Meszaros et al. |
| 4,918,074 A | 4/1990 | Tsuda et al. |
| 5,185,446 A | 2/1993 | Shaw et al. |
| 5,281,625 A | 1/1994 | Zipplies et al. |
| 5,426,186 A | 6/1995 | Shaw et al. |
| 5,612,359 A | 3/1997 | Murugesan |
| 5,631,282 A | 5/1997 | Goetz |
| 5,670,504 A | 9/1997 | Bochis et al. |
| 5,679,705 A | 10/1997 | Baker et al. |
| 5,696,156 A | 12/1997 | Baker et al. |
| 5,696,260 A | 12/1997 | Shaw et al. |
| 5,952,363 A | 9/1999 | Kristiansen et al. |
| 6,013,799 A | 1/2000 | Shaw et al. |
| 6,043,265 A | 3/2000 | Murugesan et al. |
| 6,057,329 A | 5/2000 | Davis et al. |
| 6,133,257 A | 10/2000 | Batchelor et al. |
| 6,150,356 A | 11/2000 | Lloyd et al. |
| 6,274,587 B1 | 8/2001 | Holladay et al. |
| 6,538,000 B1 | 3/2003 | Holladay et al. |
| 6,599,908 B1 | 7/2003 | Davis et al. |
| 6,632,836 B1 | 10/2003 | Baker et al. |
| 2005/0148603 A1 | 7/2005 | Jimenez et al. |
| 2005/0192283 A1 | 9/2005 | Trybulski et al. |
| 2007/0185143 A1 | 8/2007 | Traquandi et al. |

FOREIGN PATENT DOCUMENTS

| | | |
|---|---|---|
| DE | 3309432 A1 | 9/1983 |
| EP | O 163 240 A2 | 12/1985 |
| EP | O 183 848 A1 | 6/1986 |
| EP | O 217 142 A2 | 4/1987 |
| EP | O 254 119 A1 | 1/1988 |
| EP | O 304 001 A2 | 2/1989 |
| EP | 0 565 096 B1 | 10/1993 |
| GB | 1596320 | 8/1981 |
| JP | 61-227584 | 10/1986 |
| JP | 63-60985 | 3/1988 |
| JP | 63-107983 | 5/1988 |
| JP | 1-271751 | 10/1989 |
| JP | 8-301871 | 11/1996 |
| WO | WO 85/04172 | 9/1985 |
| WO | WO 90/10632 | 9/1990 |
| WO | WO92/04351 | 3/1992 |
| WO | WO 93/14083 | 7/1993 |
| WO | WO 97/35550 | 10/1997 |
| WO | WO 98/18475 | 5/1998 |
| WO | WO 98/18476 | 5/1998 |
| WO | WO98/28281 | 7/1998 |

(Continued)

OTHER PUBLICATIONS

Li G-R, Feng J, Yue L, Carrier M, Nattel S. Evidence for two components of delayed rectifier K+ current in human ventricular myocytes. Circ Res. 1996; 78:689-696.

(Continued)

Primary Examiner — James O Wilson
Assistant Examiner — Cecilia M Jaisle
(74) Attorney, Agent, or Firm — Mary K. VanAtten; Terence J. Bogie

(57) ABSTRACT

A compound of formula I wherein m, n, A, B, D, E, G, H, Y, $R^1$, $R^2$, $R^3$, $R^4$, $R^5$, and $R^8$, are described herein.

5 Claims, No Drawings

FOREIGN PATENT DOCUMENTS

| WO | WO98/58926 | 12/1998 |
|---|---|---|
| WO | WO 00/01389 | 1/2000 |
| WO | WO01/36422 | 5/2001 |
| WO | WO 03/088908 | 10/2003 |
| WO | WO2004/104007 | 12/2004 |
| WO | WO2005/037843 | 4/2005 |
| WO | WO2005/082865 | 9/2005 |

OTHER PUBLICATIONS

Feng J, Wible B, Li Gr, Wang Z, Nattel S. Antisense oligodeoxynucleotides directed against Kv1.5 mRNA specifically inhibit ultrarapid delayed rectifier K+ current in cultured adult human atrial myocytes. Circ. Res. Apr. 1997; 80(4):572-579.

Amos GJ, Wettwer E. Metzger F, Li Q, Himmel HM, Ravens U. Differences between outward currents of human atrial and subepicardial ventricular myocytes. J Physiol (Lond). 1996; 4911:31-50.

Chandy and Gutman, "Voltage-gated potassium channel genes" in Handbook of Receptors and Channels—Ligand and Voltage-gated Ion Channels, ed. R.A. North, 1995.

Doupnik et al., Curr. Opin. Neurobiol. 5:268, 1995.

Chandy et al., J. Exp. Med. 160, 369, 1984.

Price et al., Proc. Natl, Acad, Sci. USA, 86, 10171, 1989.

Leonard et al., Proc. Natl, Acad. Sci, USA, 89, 10094, 1992.

Lin et al., J. exp. Med, 177, 637, 1993.

Singh B.N., Vaughan Williams E.M. "A Third Class of Anti-Arrhythmic Action: Effects on Atrial and Ventricular Intracellular Potentials and Other Pharmacological Actions on Cardiac Muscle, of MJ 1999 and AH 3747" Br. J. Pharmacol 1970; 39:675-689.

Singh B.N., Vaughan Williams E.M, "The Effect of Amiodarone, A New Anti-Anginal Drug, on Cardiac Muscle", Br J. Pharmacol 1970; 39:657-667.

Decoursey et al., Nature, 307, 465, 1984.

Sanguinetti and Jurkiewicz, Two Components of Cardiac Delayed Rectifier K+ Current: Differential Sensitivity to Block by Class III Antiarrhythmic Agents, J Gen Physiol 1990, 96:195-215.

Balser J.R. Bennett, P.B., Hondeghem, L.M. and Roden, D.M. Suppression of Time-Dependent Outward Current in Guinea Pig Ventricular Myocytes: Actions of Quinidine and Amiodarone. Circ. Res. 1991, 69:519-529.

Nademanee, K. "The Amiodarone Odessey" .J.Am. Coll. Cardiol. 1992;20:1063-1065.

Roden, D.M. "Current Status of Class III Antiarrhythmic Drug Therapy", Am J. Cardiol, 1993; 72:44B-49B.

Hondeghem, L.M. "Development of Class III Antiarrhythmic Agents". J.Cadiovasc.Cardiol. 20 (Suppl.2):S17-S22 (1992).

Wang et al., 1993, Circ Res 73:1061-1076.

Fedida et al., 1993, Circ Res 73:210-216.

Snyders at al., 1993, J Gen Physiol 101:513-543.

Swanson et al., (1990), Neuron 4:929-939.

Vaughn Williams, E.M. "Classification of Antiarrhythmic Drugs" In Symposium on Cardiac Arrhythmias, edited by: E. Sandoe, E. Flensted-Jensen, K. Olesen; Sweden, Astra, Sodertalje, pp. 449-472, 1970.

Yang, T. et al., "Mechanism of block of a human cardiac potassium channel by terfenadine racemate and enantiomers", British J. of Pharm., vol. 115, pp. 267-274 (1995).

Grissmer S, et al., Mol Pharmacol Jun. 1994;45(6):1227-34.

Petersen KR, and Nerbonne JM, Pflugers Arch Feb. 1999;437(3):381-92.

Bowlby MR, and Levitan IB, J Neurophysiol Jun. 1995;73(6):2221-9.

Kalman K, et al., J Biol Chem Mar. 6, 1998;273(10):5851-7.

Cochran, S. M., et al. "Regionally selective alterations in local cerebral glucose utilization evoked by charybdotoxin, a blocker of central voltage-activated K+-channels", European Journal of Neuroscience, vol. 14, pp. 1455-1463 (2001).

Coleman, S. K. et al., "Subunit Composition of Kv1 Channels in Human CNS", J. Neurochem., vol. 73, No. 2, pp. 849-858 (1999).

Davies, A. R. L. et al., "Kv Channel Subunit Expression in Rat Pulmonary Arteries", Lung, vol. 179, pp. 147-161 (2001).

Frey, B. W. et al., "Blocking of cloned and native delayed rectifier K+ channels from visceral smooth muscles by phencyclidine", Neurogastroenterol. Mot., vol. 12, pp. 509-516 (2000).

Hanson, D. C. et al., "UK-78,282, a novel piperidine compound that potently blocks the Kv|1.3 voltage-gated potassium channel and inhibits human T cell activation", Brit. J. Pharmacology, vol. 126, pp. 1707-1716 (1999).

Hatton, W. J. et al., "Functional and molecular expression of a voltage dependent K+ channel (Kv1.1) in interstitial cells of Cajal", Journal of Physiology, vol. 533.2, pp. 315-327 (2001).

Koh, S. D. et al., "Contribution of delayed rectifier potassium currents to the electrical activity of murine colonic smooth muscle", J. Physiol., vol. 515.2, pp. 475-487 (1999).

Kourrich, S. et al., "Kaliotoxin, a Kv1.1 and Kv1.3 channel blocker, improves associative learning in rats", Behavioural Brain Research, vol. 120, pp. 35-46 (2001).

Lopantsev, V. et al., "Hyperexcitability of CA3 Pyramidal Cells in Mice Lacking the Potassium Channel Subunit Kv1.1", Epilepsia, vol. 44, No. 12, pp. 1506-1512 (2003).

MacDonald, P. E. et al., "Members of the Kv1 and Kv2 Voltage-Dependent K+ Channel Families Regulate Insulin Secretion", Mol. Endocrinol., vol. 15, No. 8, pp. 1423-1435 (2001).

MacDonald, P. E. et al., "Voltage-dependent K+ channels in pancreatic beta cells: Role, regulation and potential as therapeutic targets", Diabetologia, vol. 46, pp. 1046-1062 (2003).

Pozeg, Z. I. et al., "In Vivo Gene Transfer of the $O_2$-Sensitive Potassium Channel Kv1.5 Reduces Pulmonary Hypertension and Restores Hypoxic Pulmonary Vasoconstriction in Chronically Hypoxic Rats", Circulation, vol. 107, No. 15, pp. 2037-2044 (2003).

Rho, J. M. et al., "Developemental Seizure Susceptibility of Kv1.1 Potassium Channel Knockout Mice", Dev. Neurosci., vol. 21, pp. 320-327 (1999).

Shah, K. et al., "Immunosuppressive effects of a Kv1.3 inhibitor", Cellular Immunology, vol. 221, pp. 100-106 (2003).

Vianna-Jorge, R. et al., "Shaker-type Kv1 channel blockers increase the peristaltic activity of guinea-pig ileum by stimulating acetylcholine and tachykinins release by the enteric nervous system", British Journal of Pharmacology, vol. 138, pp. 57-62 (2003).

Wickenden, A. D., "Potassium channels as anti-epileptic drug targets", Neuropharmacology,. vol. 43, pp. 1055-1060 (2002).

Wulff, H. et al., "Potassium channels as therapeutic targets for autoimmune disorders", Curr. Opin. Drug Discov. Devel., vol. 6, No. 5, pp. 640-647 (2003).

Xu, J. et al., "The voltage-gated potassium channel Kv1.3 regulates peripheral insulin sensitivity", PNAS, vol. 101, No. 9, pp. 3112-3117 (2004).

Zipplies et al., 1991, CAS: 115, 8332.

Bryant et al., 1995, CAS: 123:339713.

Greene, T.W. et al., Protective groups in Organic Synthesis, Second Edition, John Wiley and Sons, publ., pp. ix-x (table of contents)(1991).

Bremner et al., "Therapy of Crohn's Disease in childhood", Expert Opin. Pharmaother., 3(7), pp. 809-825 (2002).

Singh et al., "Immune therapy in inflammatory bowel disease and models of colitis", British Journal of Surgery, 88, pp. 1558-1569 (2001).

Robinson, et el., "Medical Therapy of Inflammatory Bowel Disease for the $21^{st}$ Century", Eur. J. Surg. Suppl 582, pp. 90-98 (1998).

Ishida, J. et al., "4-Phenyl-1,2,3,6-tetrahydropyridine, an excellent fragment to improve the potency of PARP-1 inhibitors", Bioorganic & Medicinal Chemistry Letters, 15(19):4221-4225 (2005).

Yoshizumi, T. et al., "An efficient and convenient synthesis of tetrahydrocycloheptapyridines: New precursors for CNS agents", Synthesis, 10:1593-1600 (2005).

Low, J.H. et al., "3-tert-Butyl-7,7-dimethyl-1-phenyl-5,8,7,8-tetrahydroimidazo[3,4-b]quinolin-5-one and 2,8,8-trimethyl-5-phenyl-6,7,8,9-tetrahydroimidazo[2,3-a]quinolin-6-one: chains generated by C-H—N hydrogen bonds", Acta Crystallographica, Section C: Crystal Structure Communications, C60(7):o479-o482 (2004).

Drizin, I. et al., "Structure-Activity studies for a novel series of tricyclic dihydropyrimidines as KATP channel openers (KCOs)", Bioorganic & Medicinal Chemistry Letters, 12(11):1481-1484 (2002).

Rapecki, S. et al., "Inhibition of human T cell activation by novel Src kinase inhibitors is dependent upon the complexity of the signal delivered to the cell", Journal of Pharmacology and Experimental Therapeutics, 303(3):1325-1333 (2002).

Popov, S.A. et al., "Formation of an optically active 2-phenyl[1,2,4]triazolo[1,5-a]pyrimidine derivative in the reaction of (+)-3-carene-derived β-chlorovinylketone with benzylidene aminoguanidine", Mendeleev Communications, 6:226-227 (2002).

Sarac, S. et al., "4-Aryl-6,6-dimethyl-1,2,3,4,5,6,7,8-octahydroquinazoline-2,5-diones: synthesis, chromatographic resolution and pharmacological activity", Pharmazie, 56(4):298-302 (2001).

Popov, S.A. et al., "Synthesis of 2-alkyl- and 2-arylpyrimidines from β-chlorovinyl ketones of cyclopentanone type", Synthetic Communications, 31(2):233-243 (2001).

Popov, S.A. et al., "Heteroannelations with pinane-derived β-enaminoaldehyde", Heterocyclic Communications, 6(4):327-332 (2000).

Popov, S.A. et al., "Synthesis of chiral fused pyrimidines from (+)-3-carene-and limonene-derived isomeric β-enaminones", Mendeleev Communications, 3:112-114 (2000).

Saito, T. et al., "Diene-transmissive hetero-Diels-Alder reaction of cross-conjugated azatrienes: a novel and efficient method for the synthesis of ring-fused nitrogen heterocycles", Chemical Communications (Cambridge), 11:1013-1014 (1997).

Yasue, N. et al., "Studies on fused pyrimidine derivatives. XI. A facile generation and stereoselective cycloaddition reactions of 5,6-dihydro-5,6-bis(methylene)-2,4(1H,3H)-pyrimidinedione intermediate", Bulletin of the Chemical Society of Japan, 65(10):2845-2847 (1992).

Noguchi, M. et al, "Studies on fused pyrimidine derivatives. VIII. The characterization and cycloaddition reaction of 5,6-dihydro-1,3-dimethyl-6-methylene-5-[(substituted amino)methylene]-2,4(1H,3H)-pyrimidinediones", Bulletin of the Chemical Society of Japan, 63(10):2938-2944 (1990).

Elguero, J. et al., "Heterocyclic chemistry. IX. Synthesis of heterocycles from isopinocamphone", Anales de Quimica, Serie C: Quimica Organica y Bioquimica, 84(2):191-195 (1988).

Okamoto, K.T., "Total synthesis of three natural products: syncarpurea, rebeccamycin, and psammaplysin-A", dissertation, Cornell University, Ithaca, NY, Diss. Abstr. Int. B, 48(1):340 (100 pages) (1987).

Okamoto, K.T. et al., "Bioimetic syntheses of syncarpurea", Tetrahedron Letters, 25(28):2937-2940 (1984).

Hufford, C.D. et al., "Syncarpurea, a novel metabolite from *Uvaria afzelii*", Tetrahedron Letters, 25(4):371-374 (1984).

FUSED HETEROCYCLIC COMPOUNDS AS INHIBITORS OF POTASSIUM CHANNEL FUNCTION

RELATED APPLICATION

This application is a Divisional application of copending, prior application Ser. No. 11/104,856, filed on Apr. 13, 2005, which claims the benefit of U.S. Provisional Application No. 60/563,143, filed Apr. 15, 2004. The entirety of each of these applications is incorporated herein by reference.

FIELD OF THE INVENTION

The present invention provides for fused heterocyclic compounds useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such) compounds in the treatment of arrhythmia, $I_{Kur}$-associated disorders, and other disorders mediated by ion channel function.

BACKGROUND OF THE INVENTION

The ultra-rapidly activating delayed rectifier $K^+$ current ($I_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv1.5, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves opthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (Prograf) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of Kv1.3, for example, are immunosuppressive. See, Wulff et al., "Potassium channels as therapeutic targets for autoimmune disorders," Curr Opin Drug Discov Devel. 2003 September; 6(5):640-7; Shah et al., "Immunosuppressive effects of a Kv1.3 inhibitor," Cell Immunol. 2003 February; 221(2):100-6; Hanson et al., "UK-78,282, a novel piperidine compound that potently blocks the Kv1.3 voltage-gated potassium channel and inhibits human T cell activation," Br J. Pharmacol. 1999 April; 126(8): 1707-16.

Inhibitiors of Kv1.5 and other Kv1.x channels stimulate gastrointestinal motility. Thus, the compounds of the invention are believed to be useful in treating motility disorders such as reflux esophagitis. See, Frey et al., "Blocking of cloned and native delayed rectifier K channels from visceral smooth muscles by phencyclidine," Neurogastroenterol Motil. 2000 December; 12(6):509-16; Hatton et al., "Functional and molecular expression of a voltage-dependent K(+) channel (Kv1.1) in interstitial cells of Cajal," J. Physiol. 2001 Jun. 1; 533(Pt 2):315-27; Vianna-Jorge et al., "Shaker-type Kv1 channel blockers increase the peristaltic activity of guinea-pig ileum by stimulating acetylcholine and tachykinins release by the enteric nervous system," Br J. Pharmacol. 2003 January; 138(1):57-62; Koh et al., "Contribution of delayed rectifier potassium currents to the electrical activity of murine colonic smooth muscle," J. Physiol. 1999 Mar. 1; 515 (Pt 2):475-87.

Inhibitors of Kv1.5 relax pulmonary artery smooth muscle. Thus, the compounds of the invention are believed to be useful in treating hypertension and otherwise improving vascular health. See, Davies et al., "Kv channel subunit expression in rat pulmonary arteries," Lung. 2001; 179(3):147-61. Epub 2002 February 04; Pozeg et al., "In vivo gene transfer of the O2-sensitive potassium channel Kv1.5 reduces pulmonary hypertension and restores hypoxic pulmonary vasoconstriction in chronically hypoxic rats," Circulation. 2003 Apr. 22; 107(15):2037-44. Epub 2003 April 14.

Inhibitors of Kv1.3 increase insulin sensitivity. Hence, the compounds of the invention are believed to be useful in treating diabetes. See, Xu et al., "The voltage-gated potassium channel Kv1.3 regulates peripheral insulin sensitivity," Proc. Natl. Acad. Sci. U.S.A. 2004 Mar. 2; 101(9):3112-7. Epub 2004 February 23 (epublished 2004 February 23); Mac-Donald et al., "Members of the Kv1 and Kv2 voltage-dependent K(+) channel families regulate insulin secretion," Mol.

Endocrinol. 2001 August; 15(8):1423-35; MacDonald et al., "Voltage-dependent K(+) channels in pancreatic beta cells: role, regulation and potential as therapeutic targets," Diabetologia. 2003 August; 46(8):1046-62. Epub 2003 June 27.

Stimulation of Kv1.1 is believed to reduce seizure activity by hyperpolarizing neurons. Thus, the compounds of the invention are believed to be useful in treating seizures, including seizures associated with epilepsy and other neurological diseases. See, Rho et al., "Developmental seizure susceptibility of kv1.1 potassium channel knockout mice," Dev Neurosci. 1999 November; 21(3-5):320-7; Coleman et al., "Subunit composition of Kv1 channels in human CNS," J. Neurochem. 1999 August; 73(2):849-58; Lopantsev et al., "Hyperexcitability of CA3 pyramidal cells in mice lacking the potassium channel subunit Kv1.1," Epilepsia. 2003 December; 44(12):1506-12; Wickenden, "Potassium channels as anti-epileptic drug targets," Neuropharmacology. 2002 December; 43(7):1055-60.

Inhibition of Kv1.x channels improves cognition in animal models. Thus, the compounds of the invention are believed to be useful in improving cognition and/or treating cognitive disorders. See, Cochran et al., "Regionally selective alterations in local cerebral glucose utilization evoked by charybdotoxin, a blocker of central voltage-activated K+-channels," Eur J. Neurosci. 2001 November; 14(9):1455-63; Kourrich et al., "Kaliotoxin, a Kv1.1 and Kv1.3 channel blocker, improves associative learning in rats," Behav Brain Res. 2001 April 8; 120(1):35-46.

SUMMARY OF THE INVENTION

Provided is a compound of formula I

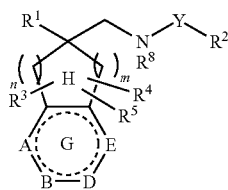

wherein, n and m are integers such that ring H, including its fusion partner, is a 5 to 7 membered ring;

A, B, D and E are —$CR^6$=, —$CR^6$—, —C(=O)—, —$NR^7$—, —N=, —O—, —S—, a bond, or a double bond, such that ring G, including atoms shared with its fusion partner, is a 5 to 6 membered ring [the moieties of A, B, D and E can be inserted into ring G in either orientation], ring G is a heterocycle wherein at least one ring atom is nitrogen, and ring G and —C(=O)—, if present, contains at least one unsaturated bond;

$R^1$ is aryl, which ring can be substituted with one or more groups of the formula —$(CH_2)_p$—$(Z^1)_q$—$(CH_2)_r$—$Z^2$;

$R^2$ is aryl, heteroaryl, cycloalkyl or heterocyclo, which ring structures can be substituted with one or more groups of the formula —$(CH_2)_p$—$(Z^1)_q$—$(CH_2)_r$—$Z^2$, which substituents may, in one or more pairs of two, together with the atoms to which they are bonded, form a carbocyclic, substituted carbocyclic, heterocyclic or substituted heterocyclic group;

Y is —C(=O)—, —C(=S)—, —C(=$NR^9$)—, —C(=$NR^{10}$)$NR^{11}$—, —C(=O)—O—, —C(=S)—O—, —C(=$NR^{12}$)—O—, —$SO_2$—, —$SO_2$—O—, or a single bond;

$R^3$, $R^4$, $R^5$, $R^6$, $R^7$, $R^8$, $R^9$, $R^{10}$, $R^{11}$ and $R^{12}$ are the same or different and are independently selected from groups of the formula —$(CH_2)_p$—$(Z^1)_q$—$(CH_2)_r$—$Z^2$; or $R^3$, $R^4$ and $R^5$ may, in one or more pairs of two (such as $R^5$ and $R^3$, $R^2$ and $R^3$, $R^3$ and $R^4$ or $R^4$ and $R^5$), together with the atoms to which they are bonded, form a carbocyclic, substituted carbocyclic, heterocyclic or substituted heterocyclic group; or $R^6$ and $R^7$ may, in one or more pairs of two, may, together with the atoms to which they are bonded, form a carbocyclic, substituted carbocyclic, heterocyclic or substituted heterocyclic group; or two occurrences of $R^6$ ($R^6$ and $R^{6*}$) may, together with the atoms to which they are bonded, form a phenyl, which may be substituted;

$Z^1$ is —$CZ^3Z^4$—, —O—, —$NZ^5$—, —S—, —SO—, —$SO_2$—, —C(O)—, —C(O)$Z^6$—, —C(O)$NZ^7$—, —C(S)—, —C(=$NOZ^8$)—, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^2$ is hydrogen, —$OZ^9$, —OC(O)$Z^{10}$, —$NZ^{11}$—C(O)—$Z^{12}$, —$NZ^{13}$—$CO_2$—$Z^{14}$, —$NZ^{15}$(C=O)—$NZ^{16}Z^{17}$, —$NZ^{18}Z^{19}$, —$NO_2$, halo, —CN, —C(O)$Z^{20}$, —$CO_2Z^{21}$, —C(S)$Z^{22}$, —(C=$NOZ^{23}$)$Z^{24}$, —C(O)$NZ^{25}Z^{26}$, —C(S)$NZ^{27}Z^{28}$, —$SZ^{29}$, —$SOZ^{30}$, —$SO_2Z^{31}$, —$SO_2NZ^{32}Z^{33}$, alkyl, substituted alkyl, alkenyl, substituted alkenyl, alkynyl, substituted alkynyl, carbocyclo, substituted carbocyclo, aryl, substituted aryl, heterocyclo (such as heteroaryl), or substituted heterocyclo, or $Z^2$ together with $Z^5$ may together with a nitrogen to which they are bonded, form a carbocyclic, substituted carbocyclic, heterocyclic or substituted heterocyclic group;

$Z^5$ is hydrogen, —C(O)$Z^{20}$, —$CO_2Z^{21}$, —C(S)$Z^{22}$, —(C=$NOZ^{23}$)$Z^{24}$, —C(O)$NZ^{25}Z^{26}$, —C(S)$NZ^{27}Z^{28}$, —$SZ^{29}$, —$SOZ^{30}$, —$SO_2Z^{31}$, —$SO_2NZ^{32}Z^{33}$, alkyl, substituted alkyl, alkenyl, substituted alkenyl, alkynyl, substituted alkynyl, carbocyclo, substituted carbocyclo, aryl, substituted aryl, heterocyclo (such as heteroaryl), or substituted heterocyclo or forms a ring with $Z^2$ as specified above;

$Z^3$, $Z^4$, $Z^6$, $Z^7$, $Z^8$, $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$, $Z^{20}$, $Z^{21}$, $Z^{22}$, $Z^{23}$, $Z^{24}$, $Z^{25}$, $Z^{26}$, $Z^{27}$, $Z^{28}$, $Z^{29}$, $Z^{30}$, $Z^{31}$, $Z^{32}$ and $Z^{33}$ are independently hydrogen, halo, alkyl, substituted alkyl, alkenyl, substituted alkenyl, alkynyl, substituted alkynyl, carbocyclo, substituted carbocyclo, aryl, substituted aryl, heterocyclo, or substituted heterocyclo; or $Z^3$, $Z^4$, $Z^6$, $Z^7$, $Z^8$, $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$, $Z^{20}$, $Z^{21}$, $Z^{22}$, $Z^{23}$, $Z^{24}$, $Z^{25}$, $Z^{26}$, $Z^{27}$, $Z^{28}$, $Z^{29}$, $Z^{30}$, $Z^{31}$, $Z^{32}$ and $Z^{33}$ (optionally $Z^3$, $Z^4$, $Z^{11}$, $Z^{12}$, $Z^{13}$, $Z^{14}$, $Z^{15}$, $Z^{16}$, $Z^{17}$, $Z^{18}$, $Z^{19}$, $Z^{23}$, $Z^{24}$, $Z^{25}$, $Z^{26}$, $Z^{27}$, $Z^{28}$, $Z^{32}$ and $Z^{33}$) may, in one or more pairs of two, together with the atoms to which they are bonded, form a carbocyclic, substituted carbocyclic, heterocyclic or substituted heterocyclic group;

p and r are independently selected from integers from 0 to 10 wherein, when q is 0, r is also 0; and q is an integer selected from 0 or 1.

By use of a respective effective amount of at least one compound described herein, provided are methods of treating (including ameliorating) or preventing arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Also provided is a method of synthesizing a compound of the invention, comprising forming a compound of formula I comprising a ring G from a compound of formula II:

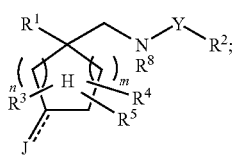

wherein J is oxo or —O—Z*, where Z* is a leaving group. The ring-forming reactions can be, for example, one of those set forth in Schemes 1-17 below (wherein —O—Z* is substituted for -OTs in Scheme 17).

DETAILED DESCRIPTION OF THE INVENTION

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. Lower alkyl groups, that is, alkyl groups of 1 to 6 carbon atoms, are generally most preferred. The term "substituted alkyl" refers to alkyl groups substituted with one or more groups (such as by groups described above in the definition of $R^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkylester" means alkyl-OC—O-alkyl or alkyl-O—CO-alkyl. The term "arylester" means aryl-OC—O-alkyl or aryl-O—CO-alkyl.

The terms "ar" or "aryl" refer to aromatic homocyclic (i.e., hydrocarbon) mono-, bi- or tricyclic ring-containing groups such as having 6 to 12 members such as phenyl, naphthyl and biphenyl. Phenyl is a preferred aryl group. The term "substituted aryl" refers to aryl groups substituted with one or more groups (such as by groups described above in the definition of $R^1$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The terms "cycloalkyl" and "cycloalkenyl" refer to mono-, bi- or tri homocylcic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups (such as by groups described above in the definition of $R^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

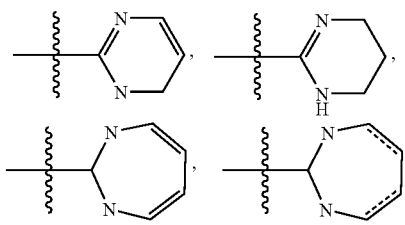

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

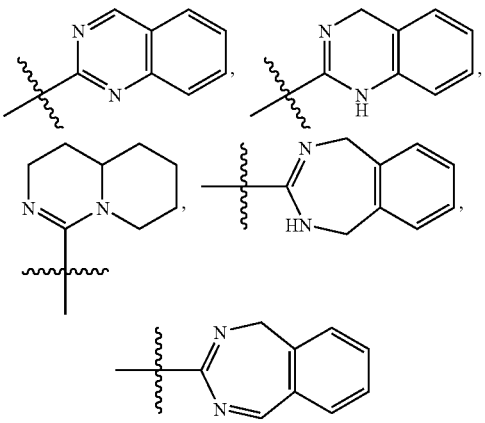

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^1$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The compounds of formula I form salts or solvates which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs, and solvates thereof, of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I can be hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The terms "including", "such as", "for example" and the like are intended to refer to exemplary embodiments and not to limit the scope of the present invention.

Exemplary Embodiments

It will be understood that any given exemplary embodiment can be combined with one or more additional exemplary embodiments.

In one embodiment of the invention, one or more of the groups according to the formula —$(CH_2)_p$—$(Z^1)_q$—$(CH_2)_r$—$Z^2$ is such that:

$Z^1$ is —$CZ^3Z^4$—, —O—, —$NZ^5$—, —S—, —SO—, —$SO_2$—, —C(O)—, —C(O)$Z^6$—, —C(O)$NZ^7$—, —C(S)—, —C(=$NOZ^8$)—, alkyl, substituted alkyl, alkenyl, substituted alkenyl, alkynyl, or substituted alkynyl; and/or $Z^2$ is hydrogen, —$OZ^9$, —OC(O)$Z^{10}$, —$NZ^5$—C(O)—$Z^{11}$, —$NZ^{12}$—$OC_2$—$Z^{13}$, —$NZ^{14}$(C=O)—$NZ^{15}Z^{16}$, —$NZ^{17}Z^{18}$, —$NO_2$, halo, —CN, —C(O)$Z^{19}$, —$CO_2Z^{20}$, —C(S)$Z^{21}$, —(C=$NOZ^{22}$)$Z^{23}$, —C(O)$NZ^{24}Z^{25}$, —C(S)$NZ^{26}Z^{27}$, —$SZ^{28}$, —$SOZ^{29}$, —$SO_2Z^{30}$, —$SO_2NZ^{31}Z^{32}$, alkyl, substituted alkyl, alkenyl, substituted alkenyl, alkynyl or substituted alkynyl, or, with respect to $R^7$ may further be aryl, substituted aryl, heteroaryl or substituted heteroaryl; and/or $Z^5$ is hydrogen, —C(O)$Z^{20}$, —$CO_2Z^{21}$, —C(S)$Z^{22}$, —(C=$NOZ^{23}$)$Z^{24}$, C(O)$NZ^{25}Z^{26}$, —C(S)$NZ^{27}Z^{28}$, —$SZ^{29}$, —$SOZ^{30}$, —$SO_2Z^{31}$, —$SO_2NZ^{32}Z^{33}$, alkyl, substituted alkyl, alkenyl, substituted alkenyl, alkynyl, substituted alkynyl, carbocyclo, substituted carbocyclo, aryl, substituted aryl, heterocyclo (such as heteroaryl), or substituted heterocyclo; and/or $Z^3, Z^6, Z^7, Z^8, Z^9, Z^{10}, Z^{11}, Z^{12}, Z^{13}, Z^{15}, Z^{16}, Z^{17}, Z^{19}, Z^{20}, Z^{21}, Z^{22}, Z^{23}, Z^{24}, Z^{25}, Z^{26}, Z^{27}, Z^{28}, Z^{29}, Z^{30}, Z^{31}, Z^{32}$ and $Z^{33}$ are independently hydrogen, halo, alkyl, substituted alkyl, alkenyl, substituted alkenyl, alkynyl, or substituted alkynyl.

In certain embodiments, ring H is a six-membered ring. In some embodiments, n=2 and m=1.

In certain embodiments, ring G is according to one of the following:

| G | A | B | D | E |
|---|---|---|---|---|
| 1 | —N= or —$NR^7$— | —N= or —$NR^7$— | —$CR^6$= or —$CR^6$— | bond |
| 2 | —$CR^6$= or —$CR^6$— | —N= or —$NR^7$— | —N= or —$NR^7$— | bond |
| 3 | —N= or —$NR^7$— | —$CR^6$= or —$CR^6$— | —N= or —$NR^7$— | bond |
| 4 | —O— | —N= or —$NR^7$— | —$CR^6$= or —$CR^6$— | bond |
| 5 | —N= or —$NR^7$— | —O— | —$CR^6$= or —$CR^6$— | bond |
| 6 | —O— | —$NR^7$— | —C(=O)— | bond |
| 7 | —$NR^7$— | —O— | —C(=O)— | bond |
| 8 | —$CR^6$= or —$CR^6$— | —N= or —$NR^7$— | —O— | bond |
| 9 | —$CR^6$= or —$CR^6$— | —O— | —N= or —$NR^7$— | bond |
| 10 | —N= or —$NR^7$— | —N= or —$NR^7$— | —S— | bond |
| 11 | —N= or —$NR^7$— | —$CR^6$= or —$CR^6$— | —S— | bond |
| 12 | —N= or —$NR^7$— | —$CR^6$= or —$CR^6$— | —N= or —$NR^7$— | —$CR^6$= or —$CR^6$— |
| 13 | —N= or —$NR^7$— | —$CR^6$= or —$CR^6$— | —$CR^6$= or —$CR^6$— | —$CR^6$= or —$CR^6$— |

In some embodiments of the invention, ring G is according to one of the following formulas (oriented with ring atoms A, B, D and E (if present) situated in counterclockwise orientation as in formula I):

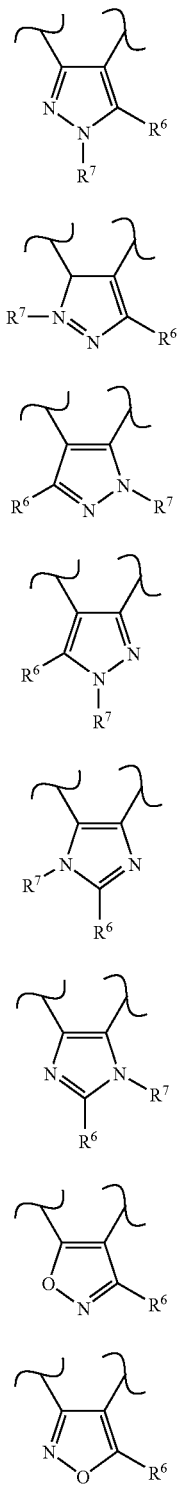
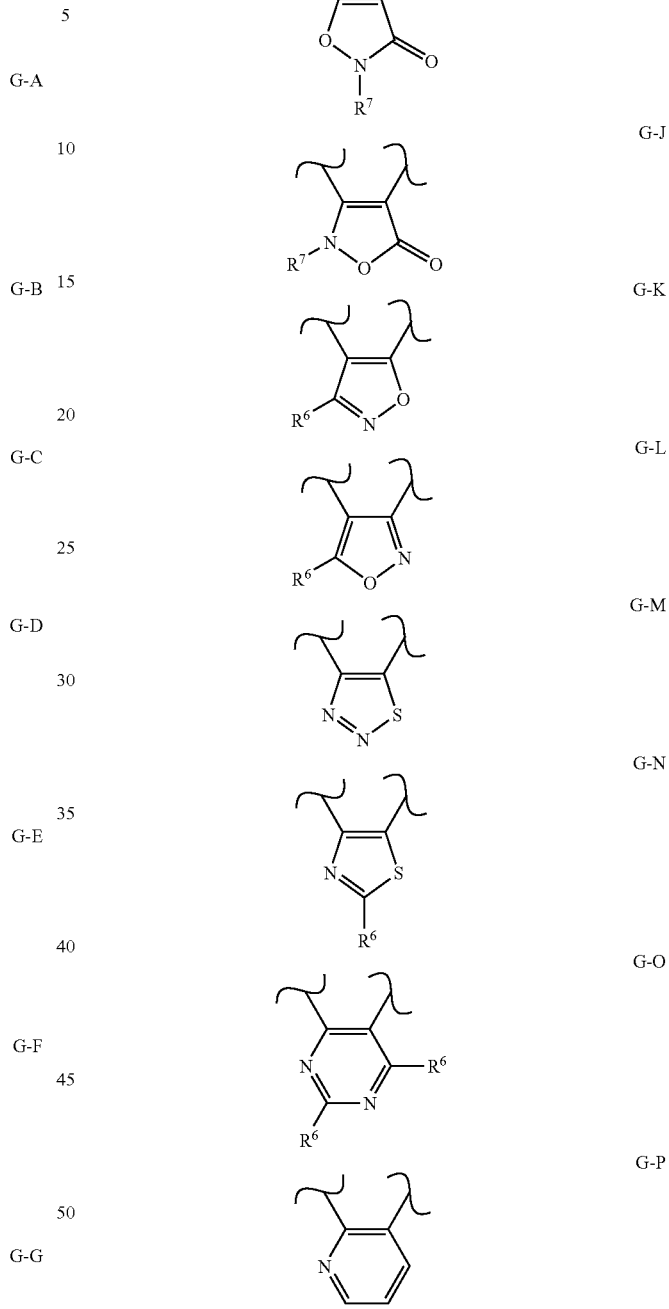

In certain embodiments, ring G is according to one of the above-listed rings further derivatized with one or more $R^7$, the ring thereby losing one degree of unsaturation and gaining one hydrogen for each such further derivatization of a ring nitrogen.

In certain embodiments, ring G is according to one of the above-listed rings with $R^6$ in rings G-C through G-H and $R^{6*}$ in ring G-O equal to hydrogen.

In certain embodiments, $R^{6*}$ in ring G-O is OH or the tautomer.

In certain embodiments, ring G is according to ring G-K. In certain embodiments, ring G is according to ring G-K wherein $R^6$ is hydrogen.

In some embodiments, ring G is a five-membered ring. In some embodiments, ring G is a six-membered ring. In some embodiments, ring G is according to formula G-H. In certain embodiments, ring G is according to:

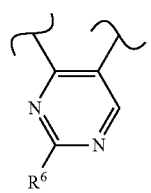

G-K*

In some embodiments, Y comprises carbonyl or thiocarbonyl or a single bond. In some embodiments, Y comprises carbonyl or a single bond. In some embodiments, Y comprises carbonyl. In some embodiments, Y comprises a single bond.

In some embodiments, $R^2$ is aryl or heteroaryl, which rings may be substituted.

The substituents on $R^1$ and $R^2$ are one or more groups of the formula $—(CH_2)_p—(Z^1)_q—(CH_2)_r—Z^2$ or according to the description of substitutions on the appropriate groups set forth above (e.g., aryl, heteroaryl, cycloalkyl, heterocyclo). In some embodiments such substituents of $R^1$ or $R^2$ may, in one or more pairs of two, together with the atoms to which they are bonded, form a carbocyclic, substituted carbocyclic, heterocyclic or substituted heterocyclic group.

In some embodiments, $R^3$, $R^4$, $R^5$, $R^6$ and $R^7$ are independently according to the description of substitutions on the appropriate groups set forth above, and such substituents may, in one or more pairs of two from among $R^3$, $R^4$ and $R^5$ or $R^6$ and $R^7$, together with the atoms to which they are bonded, form a carbocyclic, substituted carbocyclic, heterocyclic or substituted heterocyclic group.

In some embodiments, $R^8$, $R^9$, $R^{19}$, $R^{11}$ and $R^{12}$ are independently hydrogen, alkyl, substituted alkyl, alkenyl (optionally substituted), alkoxy (optionally substituted), alkanoyl (optionally substituted), or alkylester (optionally substituted).

In some embodiments, $Z^5$ is hydrogen, $—C(O)Z^{12}$ or alkyl. In some embodiments, $Z^5$ is hydrogen, alkanoyl or alkyl.

Schemes

Scheme 1

Compounds of the formula I, where A is $NR^7$ or N, B is N or $NR^7$, D is CH, and E is a single or double bond may be prepared using Scheme 1:

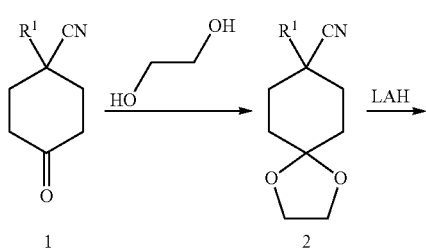

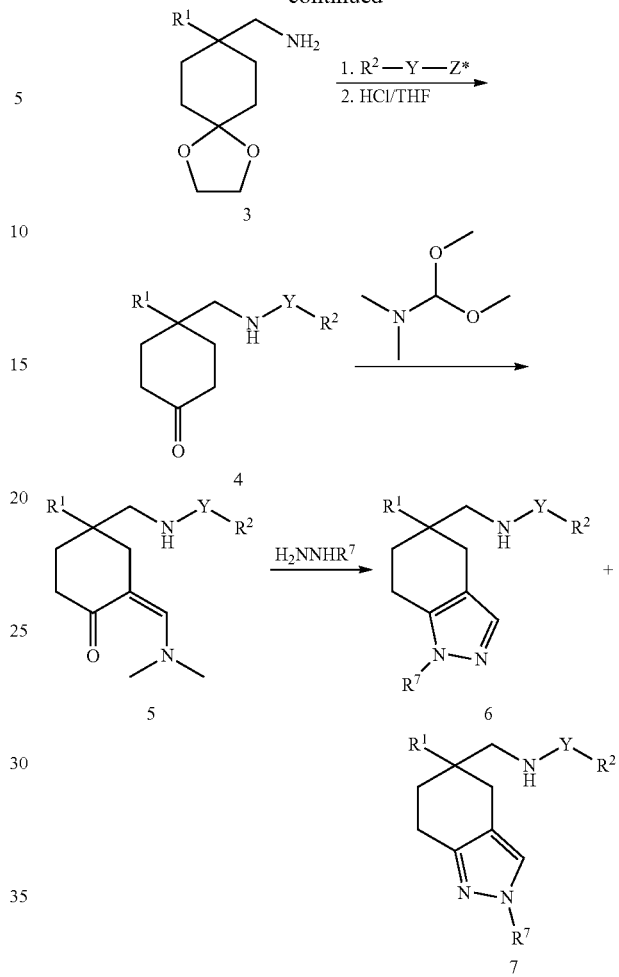

{For simplicity, ring H in this and the following schemes is shown with n=2 and m=1, and without the optional substituents $R^3$, $R^4$ and $R^5$. However, these variations can be used in the schemes.}

Compound I used in this preparation is readily prepared from commercially available reagents by methods well known to those skilled in the art and is directly commercially available when $R^1$ is phenyl. Protection of the ketone followed by reduction of the nitrile generates amine 3. Acylation, alkylation or other derivatization with $R^2$—Y—Z* (where Z* is a leaving group such as chloro) followed by ketal hydrolysis give ketone 4. Heating 4 with N,N-dimethylformamide dimethyl acetal gives 5, which is cyclized to pyrazoles 6 and 7 upon heating with hydrazines in an alcoholic solvent.

In this and other schemes, embodiments in which N is substituted with $R^8$ can be made by applying additional alkylation or acylation reactions in an appropriate order (as will be recognized by those of ordinary skill) or by driving the alkylation or acylation reactions to provide a twice derivatized amine.

Scheme 2

Compounds of the formula I, where A is O or N, B is N or O, D is CH and E is a bond, may be prepared using Scheme 2:

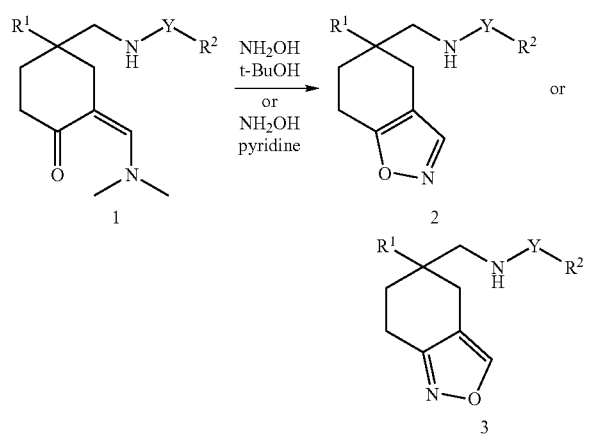

Reacting 1 with hydroxylamine in tert-butanol gives predominately isoxazole 2. Reaction of 1 with hydroxylamine in pyridine gives predominately isoxazole 3.

Scheme 3

Compounds of the formula I, where A is $NR^7$ or N, B is N or $NR^7$, D is CH and E is a single or double bond, may be prepared using Scheme 3:

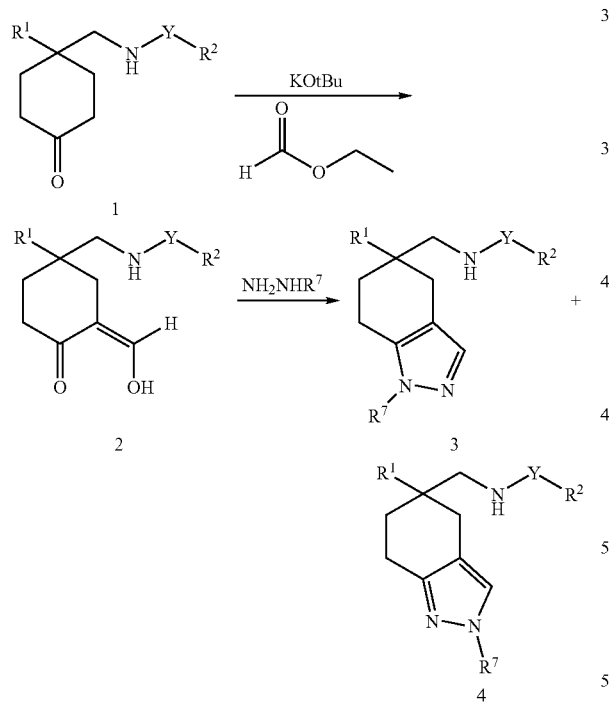

Formylation of 1 using potassium tert-butoxide and ethyl formate generates the β-dicarbonyl species 2. Heating 2 with hydrazines in an alcoholic solvent gives mixtures of pyrazoles 3 and 4.

Scheme 4

Compounds of the formula I, where A is $NR^7$ or N, B is N or $NR^7$, D is CH and E is a single or double bond, may be prepared using Scheme 4:

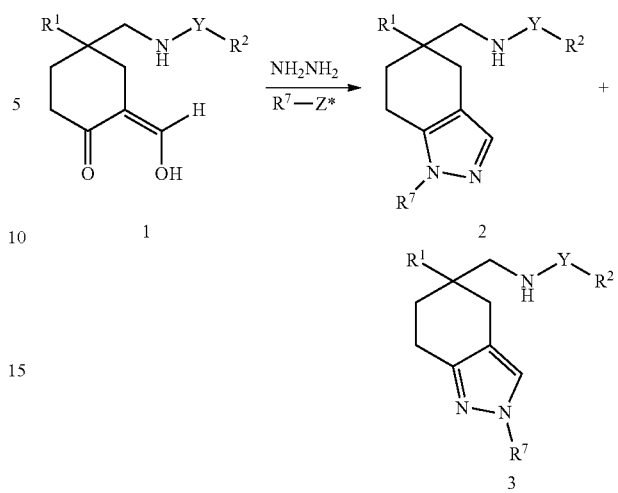

Condensation of 1 with a mixture of hydrazine and $R^7$—Z* (such as $R^{7*}$—$SO_2$—Z*) generates pyrazoles 2 and 3.

Scheme 5

Compounds of the formula I, where A is $NR^7$ or N, B is CH; D is N or $NR^7$ and E is a bond, may be prepared using Scheme 5:

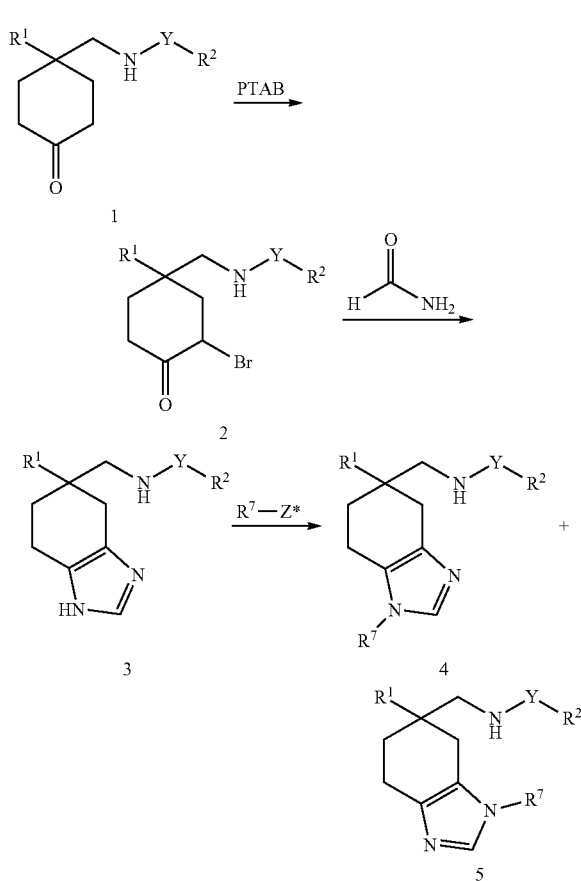

Bromination of ketone 1 gives 2. Heating 2 with formamide generates imidazole 3. An addition reaction (such as sulfonylation) gives a mixture of substituted imidazoles 4 and 5.

Scheme 6

Compounds of the formula I, where A is N, B is CR⁶, D is S and E is a bond, may be prepared using Scheme 6:

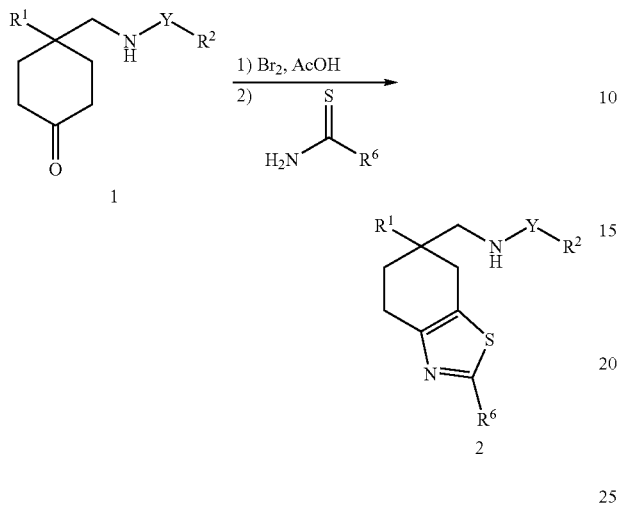

Bromination of ketone 1 in acetic acid followed by cyclization using a thioamide generates thiazole 2.

Scheme 7

Compounds of the formula I, where A is NR⁷ or N, B is N or NR⁷, D is CR⁶ and E is a single or double bond, may be prepared using Scheme 7:

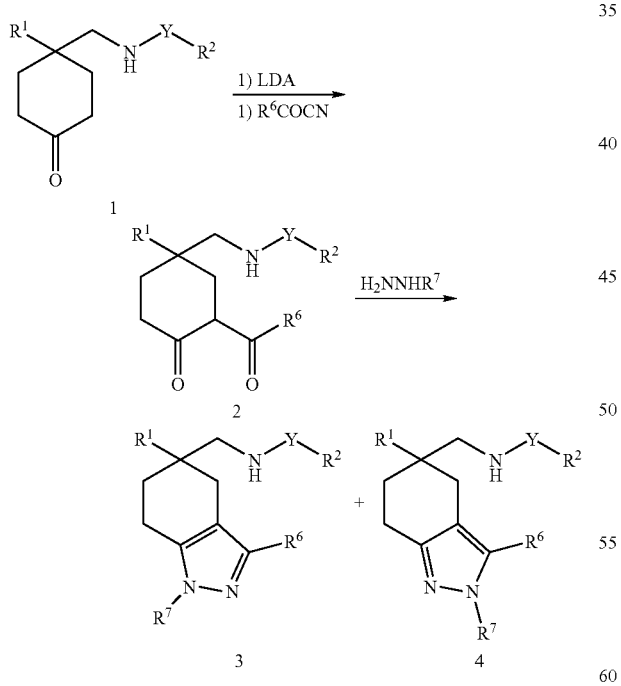

Deprotonation of 1 with LDA followed by C-acylation (see Tang et al., *Tetrahedron. Lett.* 39, 2249-2252, 1998) generates the β-dicarbonyl species 2. Heating 2 with hydrazines in an alcoholic solvent gives pyrazoles 3 and 4. Note that where R⁶ in 2 is a leaving group, 3 and 4 will have —OH in place of R⁶, which group may be tautomeric with a carbonyl form.

Scheme 8

Compounds of the formula I, where A is O or NR⁷, B is NR⁷ or O, D is C═O and E is a bond, may be prepared using Scheme 8:

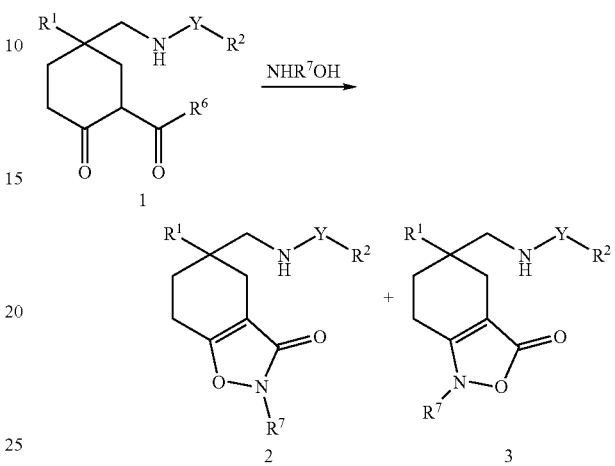

Reacting 1 with hydroxylamines in various solvents gives isoxazoles 2 and/or 3.

Scheme 9

Compounds of the formula I, where A is N, B is N, D is S and E is a bond, may be prepared using Scheme 9:

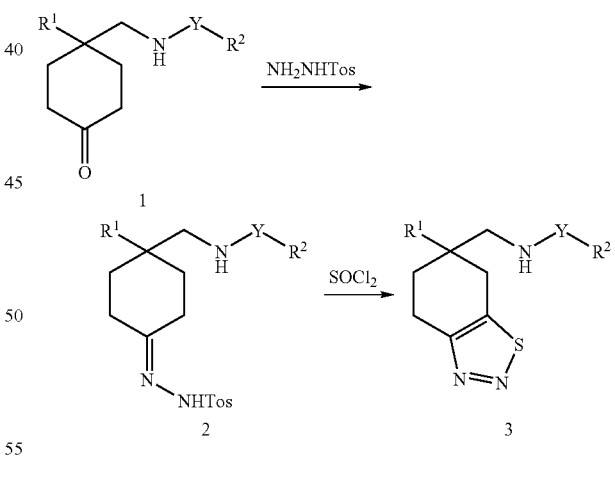

Condensation of 1 with tosylhydrazide give the hydrazone 2. Hurd-Mori cyclization (see Stanetty et al., *J. Heterocyclic Chem.* 33, 1759, 1996) generates the thiadiazole 3.

Scheme 10

Compounds of the formula I, where A is CH, B is N or NR⁷, D is NR⁷ or N, and E is a single or double bond, may be prepared using Scheme 10:

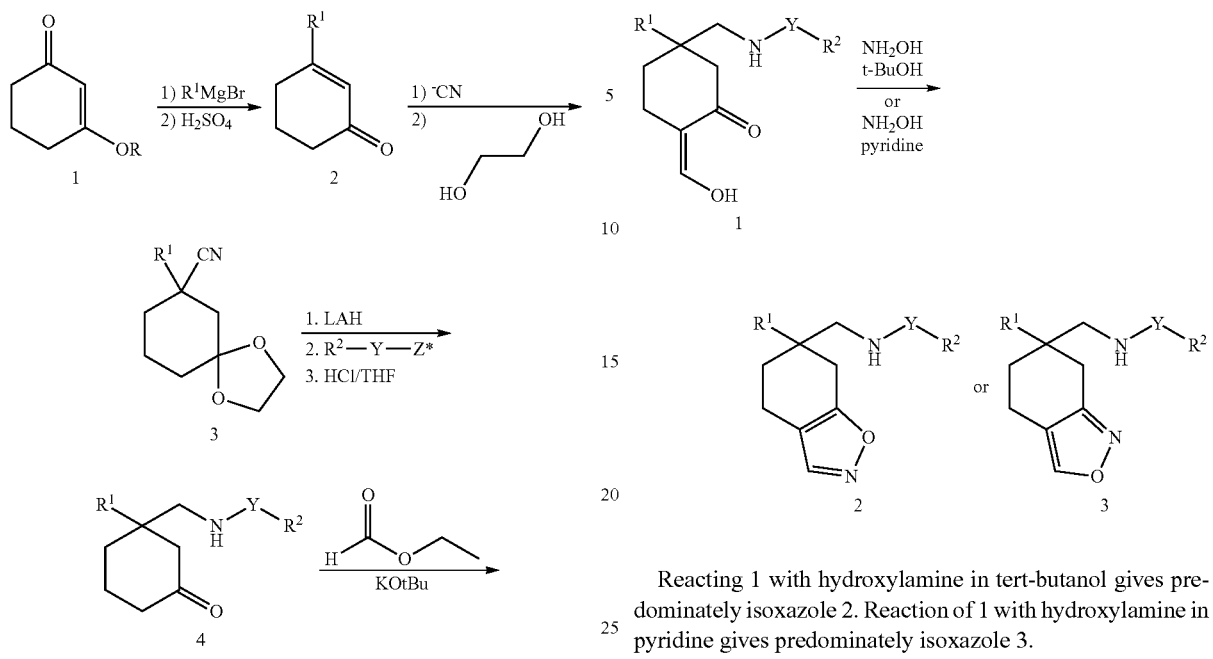

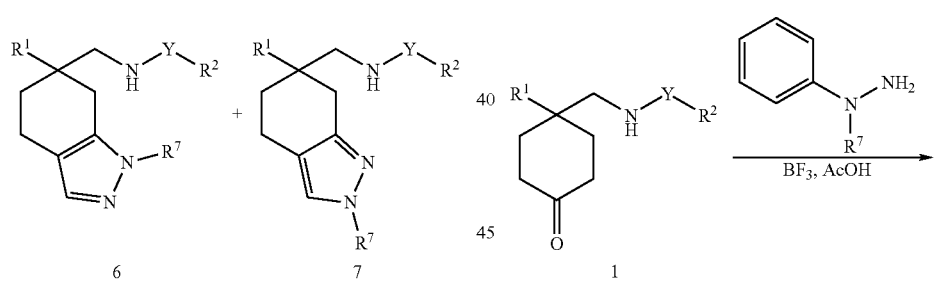

Compound 1 used in this preparation is readily prepared from commercially available reagents by methods well known to those skilled in the art and is directly commercially available when R is ethyl. Nucleophilic attack at the ketone of 1 followed by hydrolysis leads to enone 2 (see Takeda et al., Chem. Pharm. Bull. 24: 1514-26, 1976). Conjugate addition using cyanide followed by protection of the ketone gives ketal 3. Reduction of the nitrile followed by acylation and deprotection gives ketone 4. Condensation to give the β-carbonyl ketone 5 followed by cyclization using hydrazine(s) generates pyrazoles 6 and 7.

Scheme 11

Compounds of the formula I, where A is CH, B is N or O, D is O or N and E is a bond, may be prepared using Scheme 11:

Reacting 1 with hydroxylamine in tert-butanol gives predominately isoxazole 2. Reaction of 1 with hydroxylamine in pyridine gives predominately isoxazole 3.

Scheme 12

Compounds of the formula I, where A is NH, B is $CR^6$, D is $CR^{6*}$, where $CR^6$ and $CR^{6*}$ form a phenyl, which may be substituted, and E is a bond, may be prepared using Scheme 12:

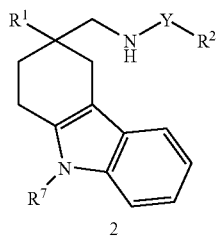

Reaction of 1 with arylhydrazines gives indole 2.

Scheme 13

Compounds of the formula I, where A is N, B is $CR^6$, D is N and E is CH may be prepared using Scheme 13:

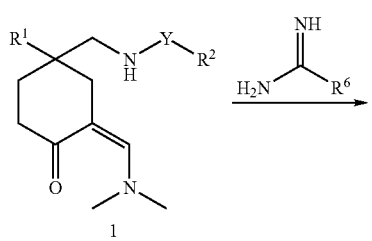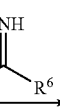

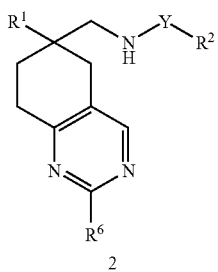

Compound 1 cyclizes to pyrimidine 2 upon heating with amidines in an alcoholic solvent.

Scheme 14

Compounds of the formula I, where A is N, B is $CR^6$, D is N and E is CH may be prepared, for example in an enantiomerically enriched fashion, using Scheme 14:

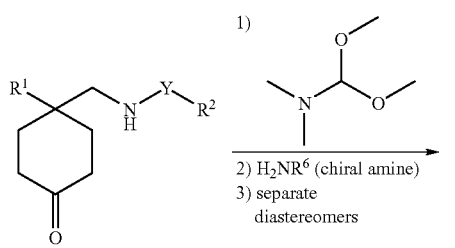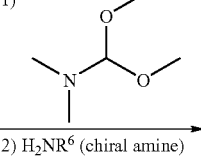

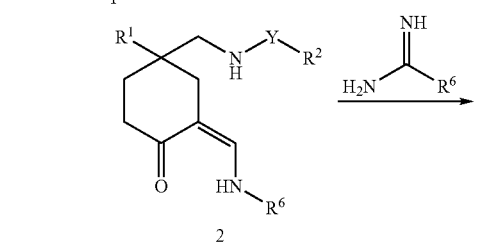

Heating 1 with N,N-dimethylformamide dimethyl acetal followed by transamination with an enantiomerically pure/enriched primary amine gives separable diastereomers of 2.

Reaction of diastereomer 2 with amidines in an alcoholic solvent generated enantiomerically pure/enriched pyrimidine 3.

Scheme 15

Compounds of the formula I, where A is N, B is $CR^6$, D is N and E is $CR^{6*}$ ($R^{6*}$ defined independently as is $R^6$) may be prepared using Scheme 15:

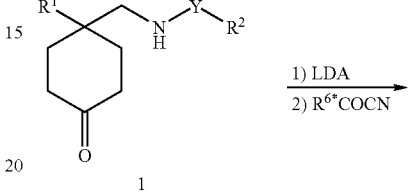

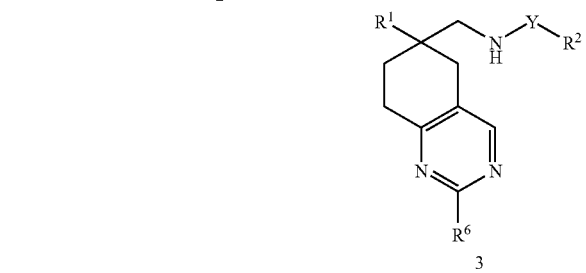

Deprotonation of 1 with LDA followed by C-acylation (see Tang et al., *Tetrahedron. Lett.* 39, 2249-2252, 1998) generates the β-dicarbonyl species 2. Heating 2 with amidines in an alcoholic solvent gives pyrimidine 3.

Scheme 16

Compounds of the formula I, where A is N, B is $CR^6$, D is $CR^{6*}$ and E is $CR^{6}$ ($R^{6}$ defined independently as is $R^6$) may be prepared using Scheme 16:

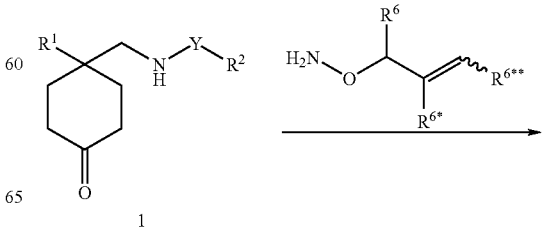

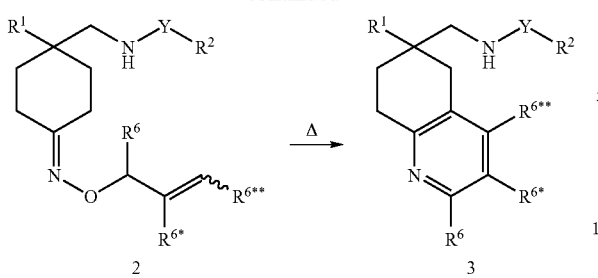

Condensation of 1 with an O-allylhydroxylamine gives the oxime 2. Thermal rearrangement of 2 (see Koyama et al., *Chem. Pharm. Bull.* 31, 2601-2606, 1983) generates pyridine 3.

Scheme 17

Compounds of the formula I, where A is C(OR$^{6\phi}$), B is N and D is O may be prepared using scheme 17. OR$^{6\phi}$) is selected from —O—(CH$_2$)$_r$—Z$^2$.

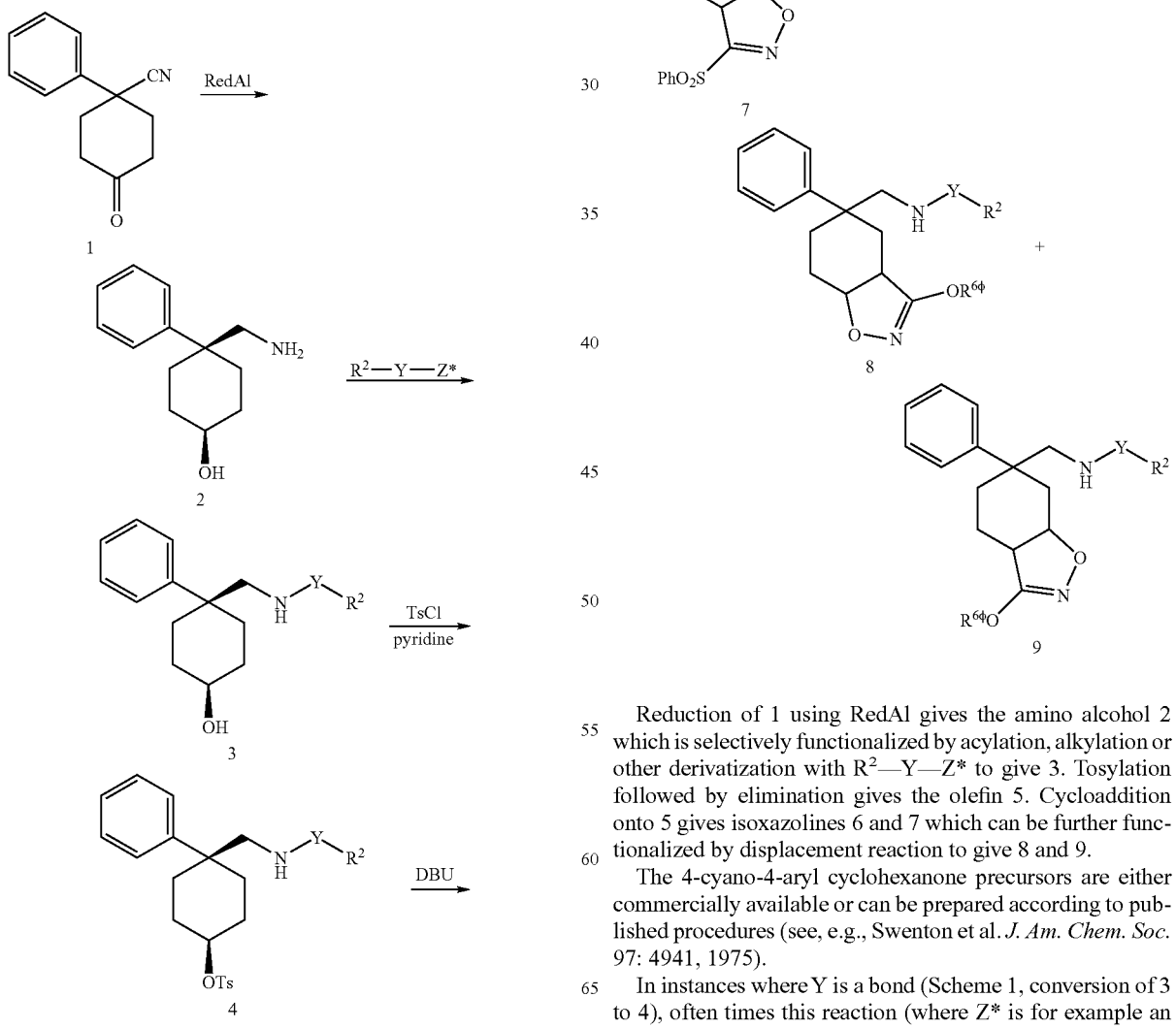

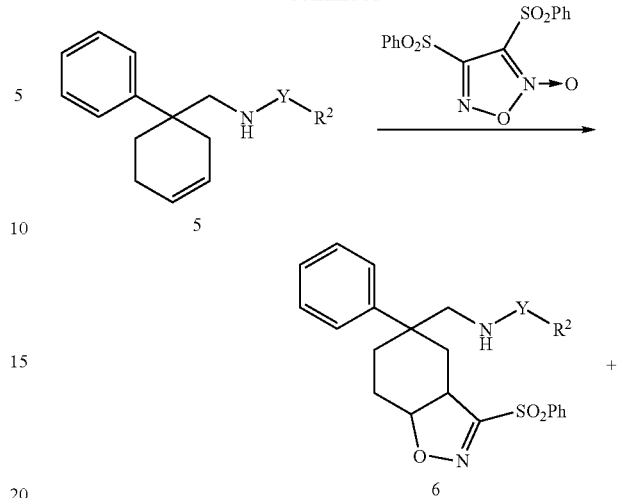

Reduction of 1 using RedAl gives the amino alcohol 2 which is selectively functionalized by acylation, alkylation or other derivatization with R$^2$—Y—Z* to give 3. Tosylation followed by elimination gives the olefin 5. Cycloaddition onto 5 gives isoxazolines 6 and 7 which can be further functionalized by displacement reaction to give 8 and 9.

The 4-cyano-4-aryl cyclohexanone precursors are either commercially available or can be prepared according to published procedures (see, e.g., Swenton et al. *J. Am. Chem. Soc.* 97: 4941, 1975).

In instances where Y is a bond (Scheme 1, conversion of 3 to 4), often times this reaction (where Z* is for example an activating group such as triflate or halogen) is catalyzed by a transition metal (usually palladium) to give N-(hetero)arylated products (see, e.g., Buchwald et al. *J. Org. Chem.* 65: 1144, 2000).

Methods describing the synthesis of fused heterocycles onto carbocyclic rings can be found for example in "Comprehensive Heterocyclic Chemistry II" Vol. 2-7, Katritzky, Rees and Scriven; 1996, Pergamon. Further examples of similar but not limiting approaches toward the synthesis of heterocycles fused to carbocyclic rings include: (a) From β-carbonylcycloalkanones (see, e.g., Peterlin-Masic et al. *Bioorg. Med. Chem. Lett.* 13, 789, 2003. Fahrenholtz et al. J. Med. Chem. 15, 1056, 1972); (b) From α-halocycloalkanones (see, e.g., Butler et al. J. Med. Chem. 30, 498, 1987; Wong et al. *Synthesis* 139, 1995); From cycloalkenes via 1,3-dipolar cycloaddition (see, e.g., Witney et al. Tetrahedron Lett. 22, 3371, 1981; More general examples (see, e.g., "1,3-Dipolar Cycloaddition Chemistry" 2 Vols. Padwa, A.; 1984, Wiley).

$R^6$, a substituent off carbon on the heterocyclic ring, can come from the reagent used for cyclization (as in Schemes 6, 13, 16) or can be incorporated prior to cyclization (as in Scheme 7) or both (as in Scheme 15). It can also be incorporated via displacement of an appropriate leaving group on the heterocycle (as in Scheme 17). Also, in many cases, one can functionalize the heterocycle at carbon via metal-halogen exchange of an appropriate halogen-substituted heterocycle or by direct deprotonation at a ring C—H followed by acylation, alkylation or other derivatization with $R^6$—Z* (see, e.g., "The Chemistry of Heterocyclic Compounds" 60 Vols. Weissberger and Taylor; 1950-, Wiley).

$R^7$, a substituent off nitrogen on the heterocyclic ring, can come from the reagent used (as in Schemes 1, 3, 7, 8, and 10) or can formed by acylation, alkylation or other derivitization with $R^7$—Z* by methods recognized by those of ordinary skill.

Utility

Compounds within the scope of the present invention inhibit the Kv1 subfamily of voltage-gated K+ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the Kv1 subfamily of voltage-gated K+ channels compounds of the present invention are useful to treat a variety of further disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolyticuremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of Kv1.5, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention block IKur, and thus may be useful in the prevention and treatment of all IKur-associated conditions. An "IKur-associated condition" is a disorder which may be prevented, partially alleviated or cured by the administration of an IKur blocker. The Kv1.5 gene is known to be expressed in stomach tissue, intestinal/colon tissue, the pulmonary artery, and pancreatic beta cells. Thus, administration of an IKur blocker can provide useful treatment for disorders such as: reflux esauphagitis, functional dispepsia, constipation, asthma, and diabetes. Additionally, Kv1.5 is known to be expressed in the anterior pituitary. Thus, administration of an IKur blocker can stimulate growth hormone secretion. IKur inhibitors can additionally be useful in cell poliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents.

The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, vioxx and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such antihypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thromin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., questran); antipoliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e., glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel. The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an IKur inhibitor are well known in the art and are described in references such as *J. Gen. Physiol*. April; 101 (4):513-43, and *Br. J. Pharmacol*. 1995 May; 115(2):267-74.

Assays to determine the degree of activity of a compound as an inhibitor of other members of the Kv1 subfamily are also well known in the art. For example, inhibition of Kv1.1, Kv1.2 and Kv1.3 can be measured using procedures described by Grissmer S, et al., *Mol Pharmacol* 1994 June; 45(6):1227-34. Inhibition of Kv1.4 can be measured using procedures described by Petersen K R, and Nerbonne J M, *Pflugers Arch* 1999 February; 437(3):381-92. Inhibition of Kv1.6 can be measured using procedures described by Bowlby M R, and Levitan I B, *J Neurophysiol* 1995 June; 73(6):2221-9. And inhibition of Kv1.7 can be measured using procedures described by Kalman K, et al., *J Biol Chem* 1998 Mar. 6; 273(10):5851-7.

The following examples further illustrate the present invention, but of course, should not be construed as in any way limiting its scope.

EXAMPLES

Example 1

Racemic 2-Methoxy-N-(5-phenyl-4,5,6,7-tetrahydro-2H-indazol-5-ylmethyl)-benzamide

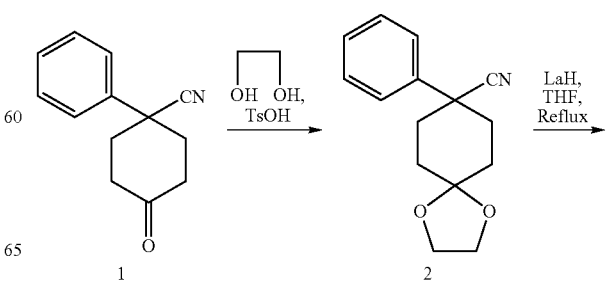

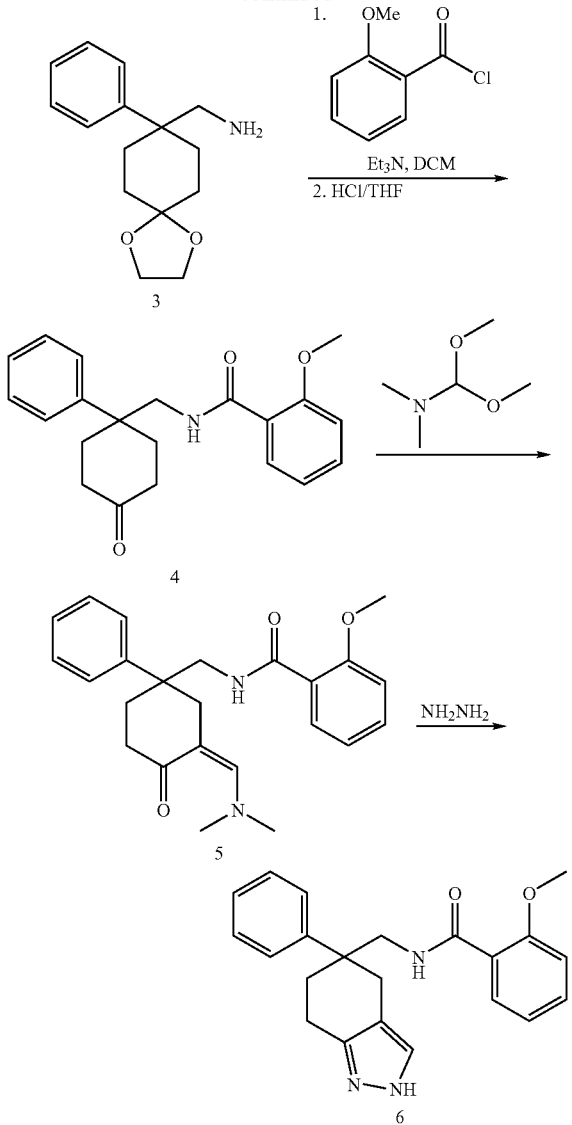

Volatiles were removed in vacuo and the residue brought up into EtOAc (200 ml) and washed with aq. NaHCO₃ (2×50 ml) and brine (50 ml). The organic layer was dried over (MgSO₄), filtered, and concentrated in vacuo to provide 2 as an oil (12.2 g, >95%), which was used in the following reaction without further purification.

Compound 3: To a solution of 2 (12.9 g, 50 mmol) in THF (100 mL) was added dropwise via cannula a 1.0 M solution of LAH in THF (60 ml, 60 mmol) The resulting solution was stirred at reflux for 2 hours then cooled to 0° C. and carefully quenched with 4N NaOH (4 mL). The mixture was filtered through a short pad of Na₂SO₄ and the filter cake washed with THF. Volatiles were removed in vacuo to provide 3 an oil (11.3 g, >90%), which was subjected to the following reaction without further purification.

Compound 4: To a solution of 3 (5.7 g, 23 mmol) in dichloromethane (100 mL) at 0° C. was added triethylamine (5.7 mL, 41 mmol) followed by dropwise addition of anisoyl chloride (4.3 ml, 29 mmol) and the resulting solution was stirred for 2.5 hours. Volatiles were removed in vacuo and the residue brought up into EtOAc (200 ml) and washed with aq. NaHCO₃ (50 ml). The organic layer was dried (MgSO₄), filtered and concentrated in vacuo. The residue was brought up into THF (50 mL) then 2N aq. HCl (50 mL) added and the resulting solution was stirred for 16 hours. The reaction mixture was diluted with EtOAc (200 ml) and washed with brine (2×50 ml), dried (MgSO₄), filtered, and volatiles removed to leave a white solid. Crystallization of this material from EtOAc/hexanes gave 4 (6.5 g, 84% yield) as a white solid. $^1$H NMR (CDCl₃, 500 mHz) δ 2.13 (m, 2H), 2.32 (m, 2H), 2.50 (m, 4H), 3.64 (s, 3H), 3.77 (s, 1H), 3.78 (s, 1H), 6.88 (d, 1H, J=8.3 Hz), 7.06 (dt, 1H, J=1.7 and 5.5 Hz), 7.42 (dt, 1H, J=1.6 and 7.2 Hz) 7.49 (m, 4H), 7.68 (bt, 1H), 8.20 (dd, 1H, J=1.7 and 8.2 Hz).

Compound 5: To a suspension of 4 (500 mg, 1.48 mmol) in DMF (0.2 mL) was added N,N-dimethylformamide dimethylacetal (0.22 mL, 1.55 mmol) and the resulting mixture was heated in a 110° C. oil bath for 20 hours. After cooling to room temperature, volatiles were removed under a stream of nitrogen then the residue placed under vacuum to leave 5 (610 mg, >90% yield) as a brown viscous oil containing trace amounts of solvent that was used without purification. [M+H]=393.

Compound 6: To a solution of 5 (55 mg, 0.14 mmol) in MeOH (0.7 mL) was added hydrazine monohydrate (0.007 mL, 0.14 mmol) and the reaction stirred for 18 hours. Volatiles were removed under a stream of nitrogen then the residue chromatographed with May 25, 1970 MeOH/hexanes/EtOAc to give 6 (23 mg, 45% yield) as a clear oil. Rt=1.42 min using Phenomenex 30×4.6 5u C18 column (Torrance, Calif.) with flow rate of 5 mL/min over 2 min gradient. 0 to 100% B. Solvent A=10/90/0.1% MeOH/H2O/TFA. Solvent B=90/10/0.1%. [M+H]=362.

Compound 1: Compound 1 is commercially available from Aldrich (Milwaukee, Wis.).

Compound 2: To a solution of 4-phenyl-4-cyano-cyclohexane-1-one 1 (10 g, 50 mmol) in toluene (200 mL) was added p-toluenesulfonic acid monohydrate (2.5 g, 13.1 mmol) followed by ethylene glycol (20 ml, 360 mmol). A Dean-Stark trap was attached and the reaction heated at reflux for 5 hours.

Example 2

Example 2 was synthesized using methodology described in example 1.

| Ex | Structure | Name | M + H |
|---|---|---|---|
| 2 | 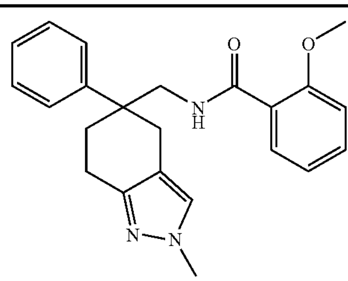 | 2-Methoxy-N-(2-methyl-5-phenyl-4,5,6,7-tetrahydro-2H-indazol-5-ylmethyl)-benzamide | 376 |

Example 3

2-Methoxy-N-(5-phenyl-4,5,6,7-tetrahydro-benzo[d]isoxazol-5-ylmethyl)-benzamide

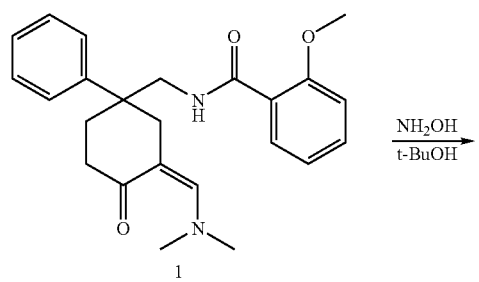

Compound 1: Compound 1 was synthesized as described in example 1.

Compound 2: To a solution of 1 (20 mg, 0.051 mmol) in hot tert-butanol (1 mL) was added hydroxylamine hydrochloride (4.1 mg, 0.06 mmol) and the reaction heated at reflux for 1.5 hours. The solution was cooled to room temperature then the solvent removed under a stream of nitrogen. The residue was purified by prep HPLC (Rt=15.2 min using a Shimadzu S5 VP-ODS 20×100 mm column (Kyoto, JP) with flow rate of 20 mL/min over 30 min gradient. 0 to 100% B. Solvent A=10/90/0.1% MeOH/H2O/TFA. Solvent B=90/10/0.1%) to give 2 (5.1 mg, 28% yield) as a clear oil. M+H=363.

Example 4

2-Methoxy-N-(5-phenyl-4,5,6,7-tetrahydro-benzo[e]isoxazol-5-ylmethyl)-benzamide

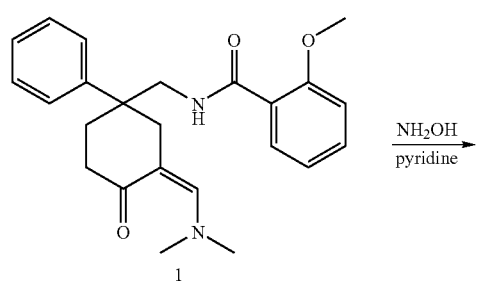

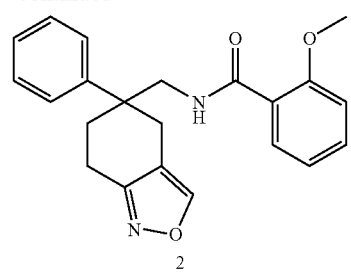

Compound 1: Compound 1 was synthesized as described in example 1.

Compound 2: To a solution of 1 (20 mg, 0.051 mmol) in pyridine (0.5 mL) was added a solution of hydroxylamine hydrochloride (8.9 mg, 0.13 mmol) in H₂O (0.050 mL) and the reaction heated at reflux for 5 hours. The solution was cooled to room temperature then the solvent removed under a stream of nitrogen. The residue was chromatographed on silica gel eluted with 50/50 EtOAc/hexanes to give 2 (8 mg, 45% yield) as a clear oil. Rt=1.61 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. M+H=363.

Examples 5 and 6

N-(1,5-Diphenyl-4,5,6,7-tetrahydro-1H-indazol-5-ylmethyl)-2-methoxy-benzamide; and N-(2,5-Diphenyl-4,5,6,7-tetrahydro-2H-indazol-5-ylmethyl)-2-methoxy-benzamide

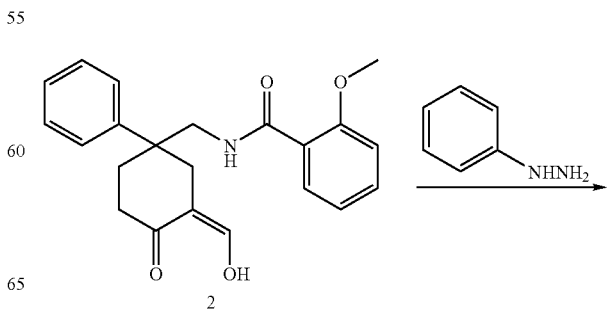

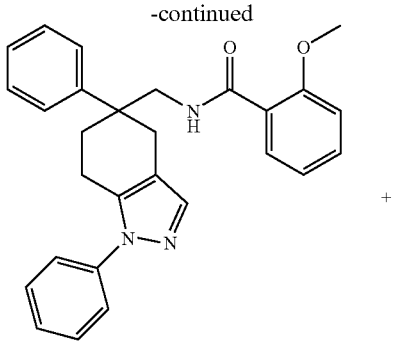

3

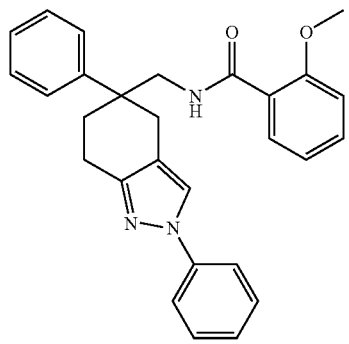

4

Compound 1: The synthesis of compound 1 is described in example 1.

Compound 2: To a flask charged with 1 (515 mg, 1.53 mmol) was added a 1.0 M solution of potassium tert-butoxide in tert-butanol (5.50 mL, 5.50 mmol) and the reaction stirred for 15 minutes turning homogeneous, then ethyl formate (0.44 mL, 5.50 mmol) was added dropwise (gas evolution) and the reaction stirred for 1 hour. The reaction was quenched by the addition of satd NH$_4$Cl (15 mL) then extracted with CHCl$_3$ (15 ml). The organic layer was washed with brine (10 mL), dried (MgSO$_4$), filtered, and concentrated in vacuo to provide 2 as a white solid (620 mg, >95%), which was used in the following reaction without further purification.

Compounds 3 and 4: To a solution of 2 (30 mg, 0.08 mmol) in MeOH (0.4 mL) was added phenylhydrazine (0.008 mL, 0.08 mmol) and the reaction stirred for 14 hours at room temperature then heated at 60° C. for 16 hours. Volatiles were removed under a stream of nitrogen then the residue was chromatographed by prep TLC eluting with 3/97 MeOH/CH$_2$Cl$_2$ (4 elutions) to give the less polar isomer 3 (10 mg, 29% yield) and the more polar isomer 4 (10 mg, 29% yield) as white solids. Rt=1.897 and 1.893 min for 3 and 4, respectively, using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=438.

Examples 7 to 13

Examples 7 to 13 were synthesized using methodology described in examples 5 and 6.

| Ex | Structure | Name | M + H |
|---|---|---|---|
| 7 | 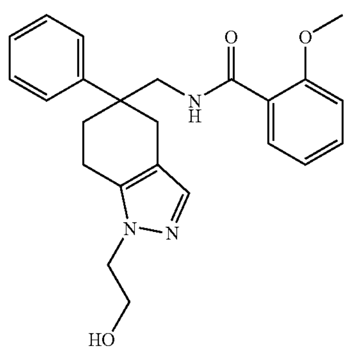 [SMILES: COc1ccccc1C(=O)NCC1(c2ccccc2)CCc2c(cnn2CCO)C1] | N-[1-(2-Hydroxy-ethyl)-5-phenyl-4,5,6,7-tetrahydro-1H-indazol-5-ylmethyl]-2-methoxy-benzamide | 406 |
| 8 | 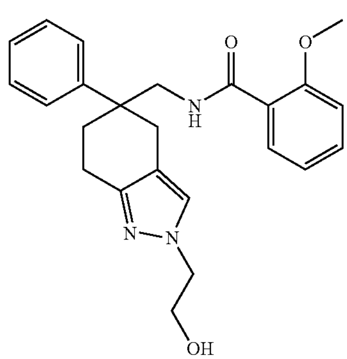 [SMILES: COc1ccccc1C(=O)NCC1(c2ccccc2)CCc2nn(CCO)cc2C1] | N-[2-(2-Hydroxy-ethyl)-5-phenyl-4,5,6,7-tetrahydro-2H-indazol-5-ylmethyl]-2-methoxy-benzamide | 406 |

-continued
| Ex | Structure | Name | M + H |
|----|-----------|------|-------|
| 9 | 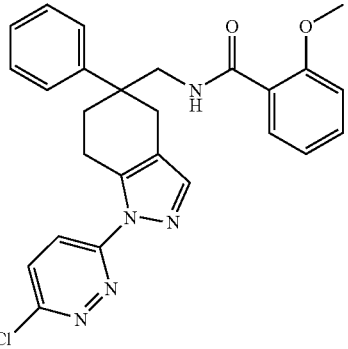 | N-[1-(6-Chloro-pyridazin-3-yl)-5-phenyl-4,5,6,7-tetrahydro-1H-indazol-5-ylmethyl]-2-methoxy-benzamide | 475 |
| 10 | 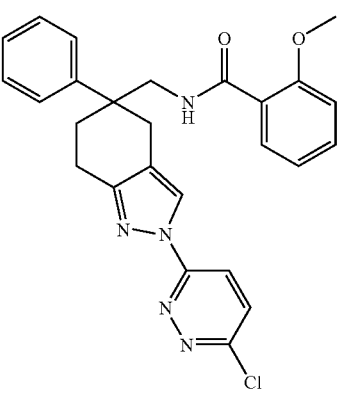 [SMILES: COc1ccccc1C(=O)NCC1(c2ccccc2)CCc2nn(-c3ccc(Cl)nn3)cc2C1] | N-[2-(6-Chloro-pyridazin-3-yl)-5-phenyl-4,5,6,7-tetrahydro-2H-indazol-5-ylmethyl]-2-methoxy-benzamide | 475 |
| 11 | 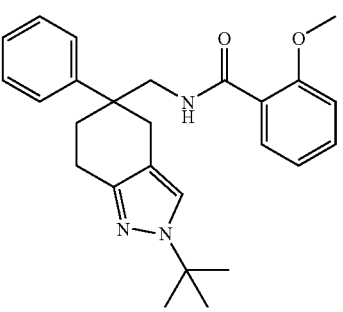 [SMILES: COc1ccccc1C(=O)NCC1(c2ccccc2)CCc2nn(C(C)(C)C)cc2C1] | N-(2-tert-Butyl-5-phenyl-4,5,6,7-tetrahydro-2H-indazol-5-ylmethyl)-2-methoxy-benzamide | 419 |
| 12 | 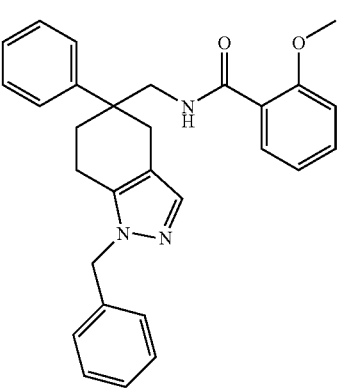 [SMILES: COc1ccccc1C(=O)NCC1(c2ccccc2)CCc2c(cnn2Cc2ccccc2)C1] | N-(1-Benzyl-5-phenyl-4,5,6,7-tetrahydro-1H-indazol-5-ylmethyl)-2-methoxy-benzamide | 453 |

| Ex | Structure | Name | M + H |
|---|---|---|---|
| 13 | 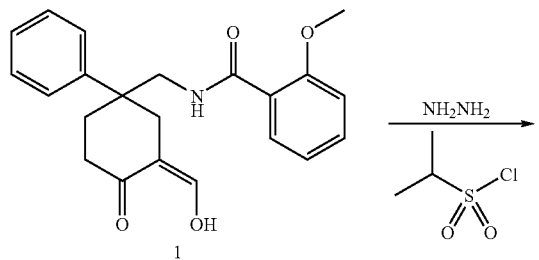 | N-(2-Benzyl-5-phenyl-4,5,6,7-tetrahydro-2H-indazol-5-ylmethyl)-2-methoxy-benzamide | 453 |

Examples 14 and 15

2-Methoxy-N-[5-phenyl-2-(propane-2-sulfonyl)-4,5,6,7-tetrahydro-2H-indazol-5-ylmethyl]-benzamide; and 2-Methoxy-N-[5-phenyl-1-(propane-2-sulfonyl)-4,5,6,7-tetrahydro-1H-indazol-5-ylmethyl]-benzamide

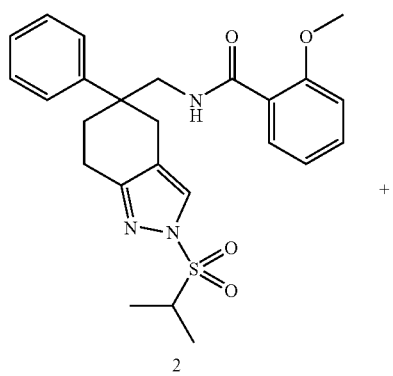

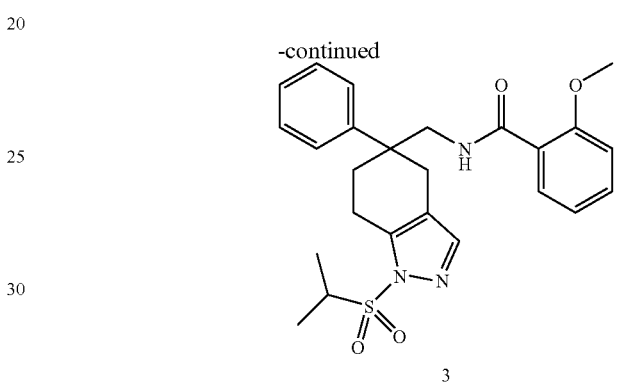

Compound 1: The synthesis of compound 1 is described in examples 5 and 6.

Compound 2: To a vial charged with hydrazine (5.4 mg, 0.17 mmol) in $CH_2Cl_2$ (0.25 mL) at 0° C. was added 2-propanesulfonylchloride (23 mg, 0.16 mmol) over a 15 minute period then the suspension stirred for 1 hour. A solution of 1 (40 mg, 0.11 mmol) in $CH_2Cl_2$ (0.20 mL) was added followed by AcOH (0.23 mL) and the reaction allowed to warm to room temperature and stirred for 16 hours. $H_2O$ (1 mL) was added and the reaction was extracted with $CH_2Cl_2$ (3×1 mL) then the combined organics washed with satd $NaHCO_3$ (1 mL), dried ($Na_2SO_4$), filtered, and concentrated in vacuo. The residue was purified by HPLC using a Phenomenex Luna 5u C18 30×250 mm preparative column (flow rate of 30 mL/min over 20 min gradient. 55 to 80% B. Solvent A=10/90/0.1% MeOH/H2O/TFA, Solvent B=90/10/0.1%) to give the more polar isomer 3 (4.4 mg, 9% yield) and the less polar isomer 2 (7.0 mg, 14% yield) as white solids. Rt=1.73 and 1.70 min for 2 and 3, respectively, using Phenomenex 30×4.6 mm 5u analytical column (flow rate of 5 mL/min over 2 min gradient. 0 to 100% B. Solvent A=10/90/0.1% MeOH/H2O/TFA. Solvent B=90/10/0.1%). [M+H]=468 for both 2 and 3.

Examples 16 to 24

Examples 16 to 24 were synthesized using methodology described in examples 14 and 15.

| Ex | Structure | Name | M + H |
|---|---|---|---|
| 16 | 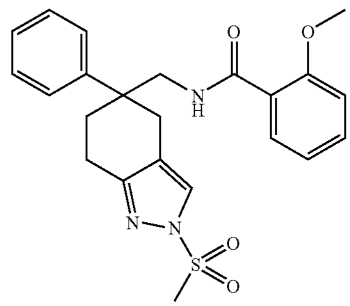 [SMILES: COc1ccccc1C(=O)NCC1(c2ccccc2)CCc2nn(S(C)(=O)=O)cc2C1] | N-(2-Methanesulfonyl-5-phenyl-4,5,6,7-tetrahydro-2H-indazol-5-ylmethyl)-2-methoxy-benzamide | 441 |
| 17 | 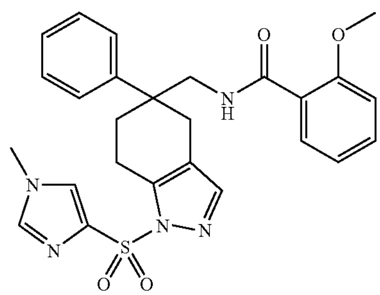 | 2-Methoxy-N-[1-(1-methyl-1H-imidazole-4-sulfonyl)-5-phenyl-4,5,6,7-tetrahydro-1H-indazol-5-ylmethyl]-benzamide | 507 |
| 18 | 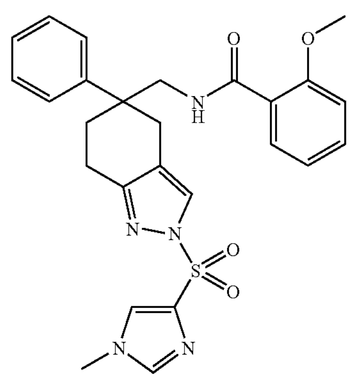 [SMILES: COc1ccccc1C(=O)NCC1(c2ccccc2)CCc2nn(S(=O)(=O)c3cn(C)cn3)cc2C1] | 2-Methoxy-N-[2-(1-methyl-1H-imidazole-4-sulfonyl)-5-phenyl-4,5,6,7-tetrahydro-2H-indazol-5-ylmethyl]-benzamide | 507 |
| 19 | 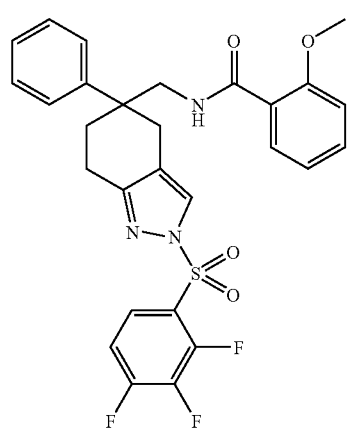 [SMILES: COc1ccccc1C(=O)NCC1(c2ccccc2)CCc2nn(S(=O)(=O)c3ccc(F)c(F)c3F)cc2C1] | 2-Methoxy-N-[5-phenyl-2-(2,3,4-trifluoro-benzenesulfonyl)-4,5,6,7-tetrahydro-2H-indazol-5-ylmethyl]-benzamide | 557 |

-continued

| Ex | Structure | Name | M + H |
|---|---|---|---|
| 20 | 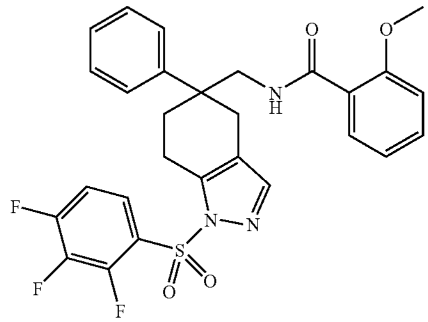 [SMILES: COc1ccccc1C(=O)NCC1(c2ccccc2)CCc2c(cnn2S(=O)(=O)c2ccc(F)c(F)c2F)C1] | 2-Methoxy-N-[5-phenyl-1-(2,3,4-trifluoro-benzenesulfonyl)-4,5,6,7-tetrahydro-1H-indazol-5-ylmethyl]-benzamide | 557 |
| 21 | 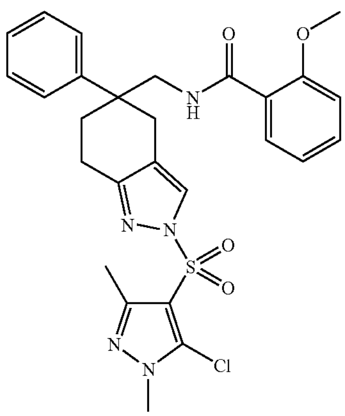 [SMILES: COc1ccccc1C(=O)NCC1(c2ccccc2)CCc2nn(S(=O)(=O)c3c(C)nn(C)c3Cl)cc2C1] | N-[2-(5-Chloro-1,3-dimethyl-1H-pyrazole-4-sulfonyl)-5-phenyl-4,5,6,7-tetrahydro-2H-indazol-5-ylmethyl]-2-methoxy-benzamide | 555 |
| 22 | 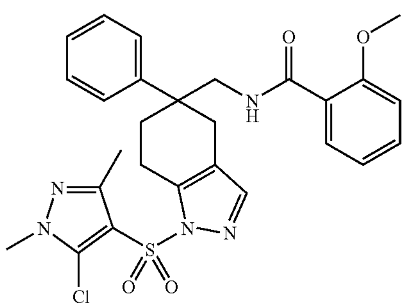 | N-[1-(5-Chloro-1,3-dimethyl-1H-pyrazole-4-sulfonyl)-5-phenyl-4,5,6,7-tetrahydro-1H-indazol-5-ylmethyl]-2-methoxy-benzamide | 555 |
| 23 | 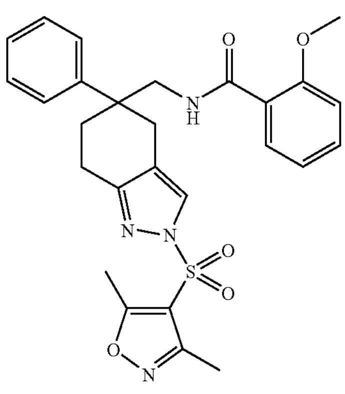 [SMILES: COc1ccccc1C(=O)NCC1(c2ccccc2)CCc2nn(S(=O)(=O)c3c(C)noc3C)cc2C1] | N-[2-(3,5-Dimethyl-isoxazole-4-sulfonyl)-5-phenyl-4,5,6,7-tetrahydro-2H-indazol-5-ylmethyl]-2-methoxy-benzamide | 522 |

| Ex | Structure | Name | M + H |
|---|---|---|---|
| 24 | 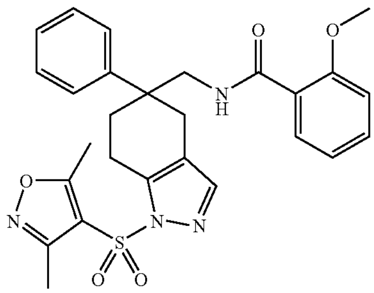 [SMILES: COc1ccccc1C(=O)NCC1(c2ccccc2)CCc2c(cnn2S(=O)(=O)c2c(C)noc2C)C1] | N-[1-(3,5-Dimethyl-isoxazole-4-sulfonyl)-5-phenyl-4,5,6,7-tetrahydro-1H-indazol-5-ylmethyl]-2-methoxy-benzamide | 522 |

Example 25

2-Methoxy-N-(5-phenyl-4,5,6,7-tetrahydro-1H-benzoimidazol-5-ylmethyl)-benzamide

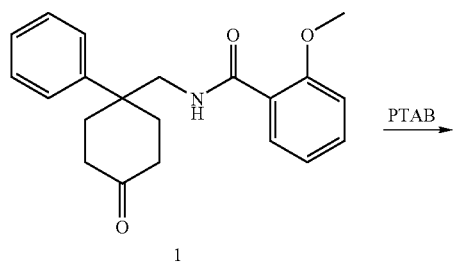

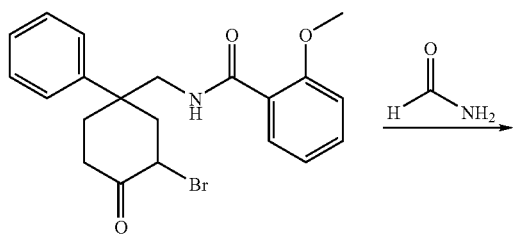

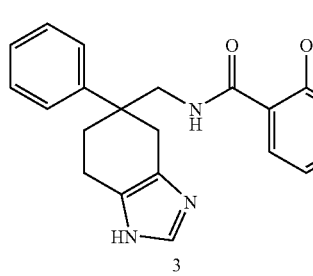

Compound 1: The synthesis of compound 1 is described in example 1.

Compound 2: To a solution of 1 (450 mg, 1.33 mmol) in THF (10 mL) at 0° C. was added a cooled (0° C.) solution of phenyltrimethylammonium tribromide (552 mg, 1.47 mmol) in THF (5 mL) rapidly via cannula and the reaction stirred for 15 minutes, turning from orange to a pale yellow. The reaction was poured into brine (50 mL) and extracted with $Et_2O$ (2×50 mL), dried ($MgSO_4$), filtered and concentrated in vacuo to leave 3 (550 mg, >95% yield) as a white solid which was used in the following reaction without further purification.

Compound 3: To a vial charged with 1 (295 mg, 0.71 mmol) was added formamide (3 mL) then the reaction sealed and heated in a 180° C. oil-bath for 1.5 hours. The solution was cooled to room temperature, 0.5 N HCl (6 mL) added, then extracted with $CH_2Cl_2$ (2×6 mL). To the aqueous layer was added ammonium hydroxide until a pH of 9 was reached, then extracted with EtOAc (2×6 mL). The organics were dried ($MgSO_4$), filtered and concentrated in vacuo to leave 3 (47 mg, 18% yield) as a pale yellow viscous oil. Rt=2.29 min using a Phenomenex 30×4.6 5u column with flow rate of 4 mL/min over 4 min gradient. 0 to 100% B. Solvent A=10/90/0.1% MeOH/H2O/H3PO4. Solvent B=90/10/0.1%.

Examples 26 and 27

N-[1-(3,5-Dimethyl-isoxazole-4-sulfonyl)-5-phenyl-4,5,6,7-tetrahydro-1H-benzoimidazol-5-ylmethyl]-2-methoxy-benzamide; and N-[3-(3,5-Dimethyl-isoxazole-4-sulfonyl)-5-phenyl-4,5,6,7-tetrahydro-3H-benzoimidazol-5-ylmethyl]-2-methoxy-benzamide

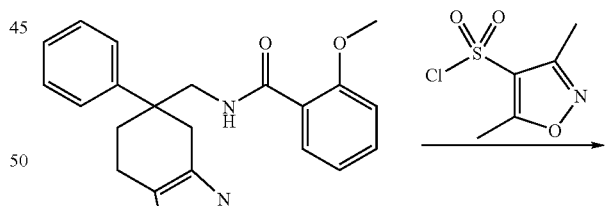

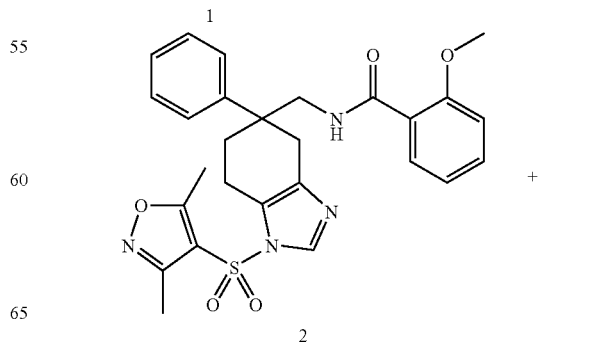

47

-continued

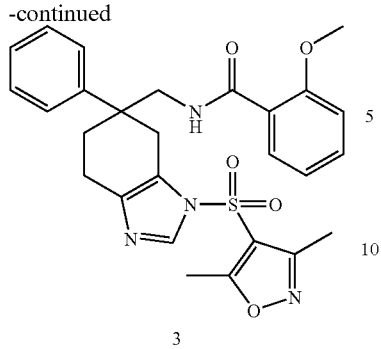

3

Compound 1: Compound 1 was synthesized as described in example 25.

Compounds 2 and 3: To a solution of 1 (22 mg, 0.061 mmol) in CH₂Cl₂ (0.2 mL) was added triethylamine (0.017 mL, 0.12 mmol) followed by 3,5-dimethylisoxazole-4-sulfonyl chloride (11.9 mg, 0.061 mmol) and the reaction stirred for 1 hour. Volatiles were removed under stream of nitrogen and the residue purified by prep TLC eluted with May 45, 1950 MeOH/EtOAc/CH₂Cl₂ to give the less polar diastereomer 2 (3.5 mg, 11% yield) and more polar diastereomer 3 (7.5 mg, 23% yield) as white solids. Rt of 2 and 3 was 1.76 and 1.74 min respectively, using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=521 for both 2 and 3.

Examples 28 and 29

Examples 28 and 29 were synthesized using methodology described in examples 26 and 27.

48

Example 30

N-(2-Amino-6-phenyl-4,5,6,7-tetrahydro-benzothiazol-6-ylmethyl)-2-methoxy-benzamide

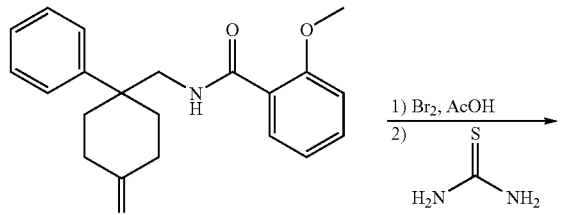

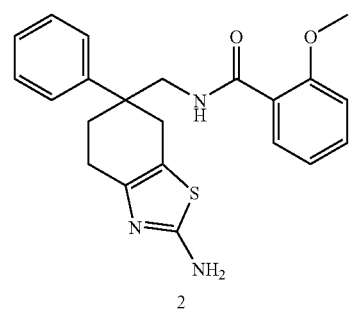

Compound 1: The synthesis of compound 1 is described in example 1.

Compound 2: To a solution of 1 (54 mg, 0.16 mmol) in AcOH (0.25 mL) at 60° C. was added Br₂ (26 mg, 0.16 mmol), the reaction stirred for 1 hour, then thiourea (24 mg, 0.32 mmol) added and the reaction heated at reflux for 1 hour. The solution was cooled to room temperature then the solvent removed under a stream of nitrogen. The residue was purified by prep TLC eluted with Jan. 5, 1994 AcOH/MeOH/CHCl₃ to

| Ex | Structure | Name | M + H |
|----|-----------|------|-------|
| 28 | 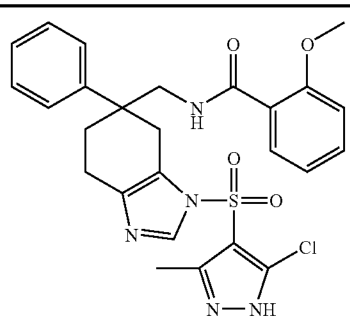 | N-[3-(5-Chloro-3-methyl-1H-pyrazole-4-sulfonyl)-5-phenyl-4,5,6,7-tetrahydro-3H-benzoimidazol-5-ylmethyl]-2-ethoxy-benzamide | 555 |
| 29 | | N-[1-(5-Chloro-1,3-dimethyl-1H-pyrazole-4-sulfonyl)-5-phenyl-4,5,6,7-tetrahydro-1H-benzoimidazol-5-ylmethyl]-2-methoxy-benzamide | 555 | give 2 (3.5 mg, 11% yield) as a white solid. Rt=1.40 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. M+H=394.

Example 31

N-(2-Acetylamino-6-phenyl-4,5,6,7-tetrahydro-benzothiazol-6-ylmethyl)-2-methoxy-benzamide

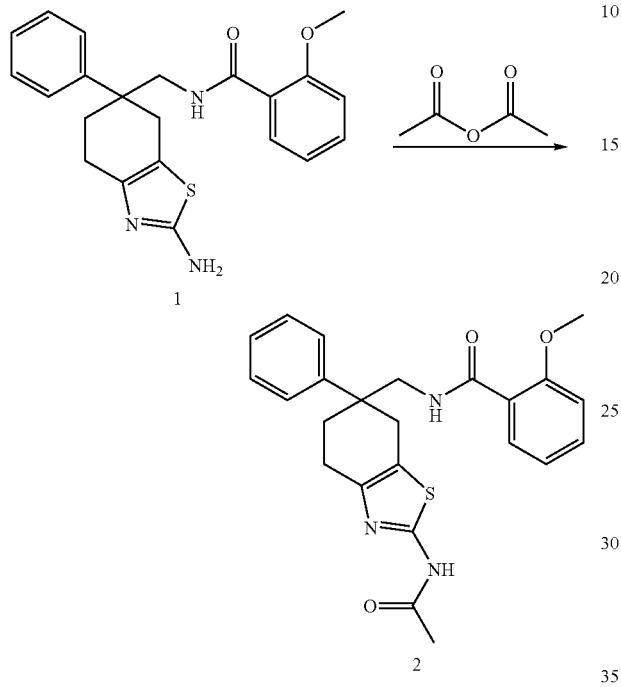

Compound 1: The synthesis of compound 1 is described in example 30.

Compound 2: To a vial charged with 1 (10 mg, 0.025 mmol) was added acetic anhydride (0.10 mL) and the reaction placed in an oil-bath at 60° C. for 0.5 hours. The reaction was cooled to room temperature, ice (1 g) added and the reaction extracted with $CHCl_3$ (3×1 mL). The organics were dried ($Na_2SO_4$), filtered and concentrated in vacuo. The residue was purified on silica gel gradiently eluted with 0 to 100% EtOAc/hexanes to give 2 (8.9 mg, 80% yield) as a white solid. Rt=1.64 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=436.

Example 32

N-(2-Diacetylamino-6-phenyl-4,5,6,7-tetrahydro-benzothiazol-6-ylmethyl)-2-methoxy-benzamide

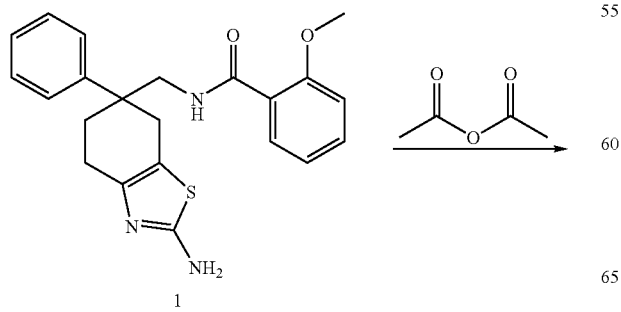

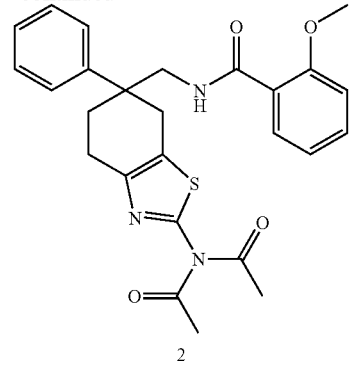

Compound 1: The synthesis of compound 1 is described in example 30.

Compound 2: To a vial charged with 1 (10 mg, 0.025 mmol) was added acetic anhydride (0.10 mL) and the reaction placed in an oil-bath at 160° C. for 0.5 hours. The reaction was cooled to room temperature, ice (1 g) added and the reaction extracted with $CHCl_3$ (3×1 mL). The organics were dried ($Na_2SO_4$), filtered and concentrated in vacuo. The residue was purified on silica gel gradiently eluted with 0 to 100% EtOAc/hexanes to give 2 (3.8 mg, 32% yield) as a white solid. Rt=1.67 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=478.

Example 33

2-Methoxy-N-(3-methyl-5-phenyl-4,5,6,7-tetrahydro-1H-indazol-5-ylmethyl)-benzamide

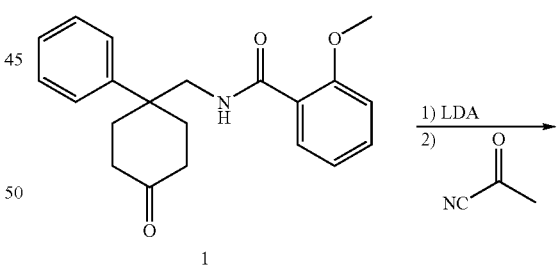

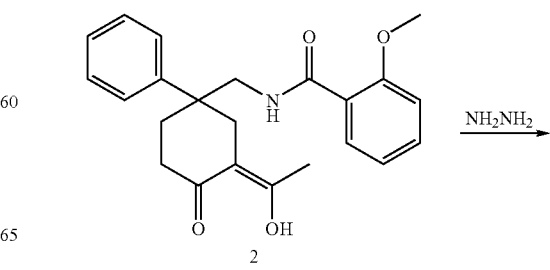

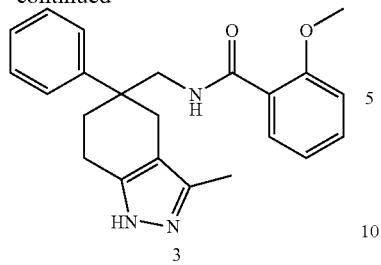

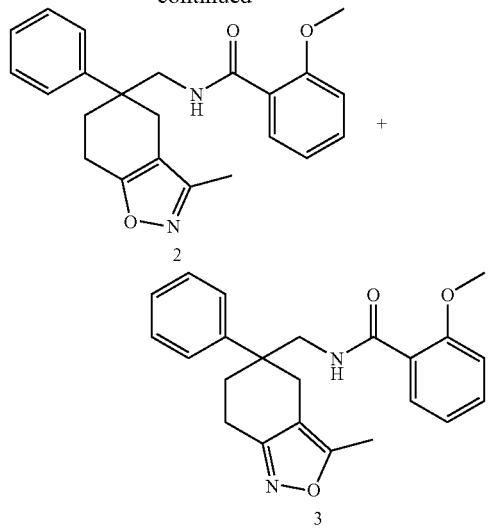

Compound 1: The synthesis of 1 is described in example 1.

Compound 2: To a solution of 1 (426 mg, 1.26 mmol) in THF (6 mL) at −78° C. was added dropwise a 1.8 M solution of LDA in THF (1.54 mL, 2.78 mmol) and the reaction stirred for 1 hour, then pyruvonitrile (0.208 mL, 2.78 mmol) was added dropwise and the reaction was stirred for 15 minutes turning homogeneous. The reaction was quenched by the addition of satd. NH₄Cl (10 mL), the layers separated, and the aqueous extracted with Et₂O (3×10 mL). The combined organics were dried (MgSO₄), filtered and concentrated in vacuo. The residue was purified on silica gel gradiently eluted with 20 to 40% EtOAc/hexanes to give 2 (230 mg, 48% yield) as an off-white solid. Rt=1.71 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=380.

Compound 3: To a vial charged with 2 (20 mg, 0.053 mmol) in MeOH (0.3 mL) was added hydrazine (0.002 mL, 0.06 mmol) and the reaction stirred for 1 hour then volatiles removed under stream of nitrogen. The residue was purified on silica gel gradiently eluted with 75 to 100% EtOAc/hexanes to give 3 (10 mg, 50% yield) as a white solid. Rt=1.43 min using Phenomenex 30×4.6 5u column with flow rate of 5 mL/min over 2 min gradient. 0 to 100% B. Solvent A=10/90/ 0.1% MeOH/H2O/TFA. Solvent B=90/10/0.1%. [M+H]= 376.

Compound 1: The synthesis of 1 was described in example 33.

Compounds 2 and 3: To a solution of 1 (20 mg, 0.054 mmol) in hot tert-butanol (0.75 mL) was hydroxylamine hydrochloride (4.1 mg, 0.060 mmol) and the reaction heated at reflux for 1.5 hours. The solution was cooled to room temperature then the solvent removed under a stream of nitrogen. The residue was purified by prep HPLC (Rt for 2 and 3=2.25 and 2.48 min, respectively) using a YMC S5 ODS 30×100 mm column (YMC, Kyoto, Japan, available from Waters, Milford, Mass.) with flow rate of 40 mL/min over 12 min gradient. 55 to 65% B. Solvent A=10/90/0.1% MeOH/ H2O/TFA. Solvent B=90/10/0.1%) to give 2 (9.7 mg, 50% yield) and 3 (4.8 mg, 25% yield) as a white solids.

Example 36

2-Methoxy-N-(3-oxo-5-phenyl-2,3,4,5,6,7-hexahydro-1H-indazol-5-ylmethyl)-benzamide Examples 34 and 35

2-Methoxy-N-(3-methyl-5-phenyl-4,5,6,7-tetrahydro-benzo[d]isoxazol-5-ylmethyl)-benzamide; and
2-Methoxy-N-(3-methyl-5-phenyl-4,5,6,7-tetrahydro-benzo[c]isoxazol-5-ylmethyl)-benzamide

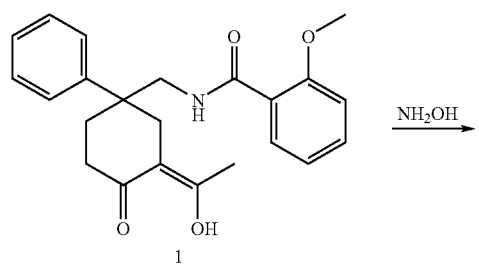

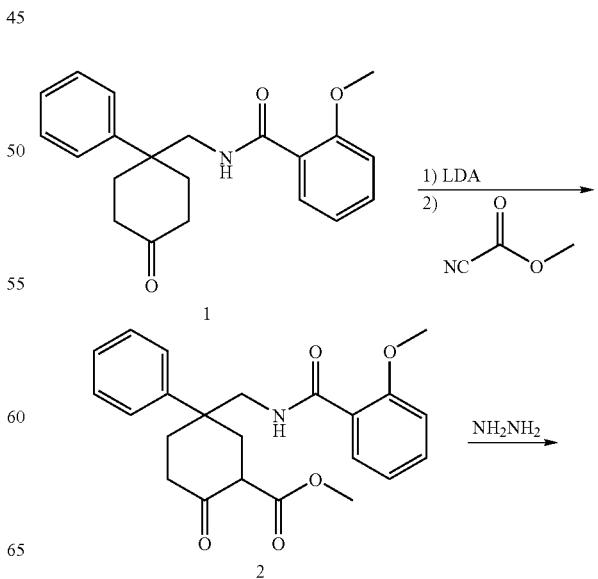

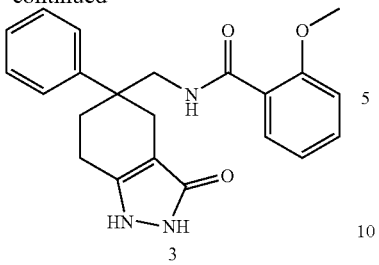

3

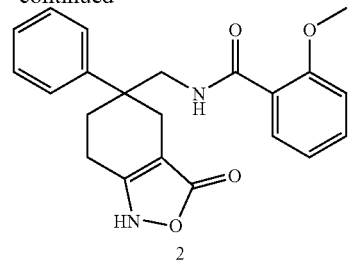

2

Compound 1: The synthesis of 1 was described in example 1.

Compound 2: To a solution of 1 (473 mg, 1.40 mmol) in THF (6.5 mL) at −78° C. was added dropwise a 1.8 M solution of LDA in THF (1.71 mL, 3.08 mmol) and the reaction stirred for 1 hour, then methylcyanoformate (0.244 mL, 3.08 mmol) added dropwise and the reaction was stirred for 1 hour. The reaction was quenched by the addition of satd NH₄Cl (10 mL), the layers separated, and the aqueous extracted with Et₂O (3×10 mL). The combined organics were dried (MgSO₄), filtered and concentrated in vacuo. The residue was purified on silica gel gradiently eluted with 20 to 30% EtOAc/hexanes to give 2 (153 mg, 28% yield) as an off-white solid. Rt=1.83 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=396.

Compound 3: To a solution of 2 (12 mg, 0.030 mmol) in MeOH (0.2 mL) was added hydrazine (0.001 mL, 0.033 mmol) and the reaction stirred for 3.5 hours then volatiles removed under stream of nitrogen. The residue was purified by prep TLC eluted with 5% MeOH/CH₂Cl₂ to give 3 (6 mg, 50% yield) as a white solid. Rt=1.41 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=378.

Compound 1: The synthesis of 1 was described in example 36.

Compound 2: To a vial charged with hydroxylamine hydrochloride (5.7 mg, 0.082 mmol) and sodium acetate trihydrate (1.8 mg, 0.013 mmol) was added a solution of 1 (17 mg, 0.043 mmol) in EtOH (0.3 mL) and the reaction heated at 80° C. for 4 hours. The reaction was cooled to room temperature, volatiles removed under stream of nitrogen, then the residue was purified on silica gel gradiently eluted with 1 to 10% MeOH/CH₂Cl₂ to give 2 (14 mg, 80% yield) as a white solid. Rt=1.53 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=379.

Example 38

2-Methoxy-N-(1-methyl-3-oxo-5-phenyl-1,3,4,5,6,7-hexahydro-benzo[c]isoxazol-5-ylmethyl)-benzamide

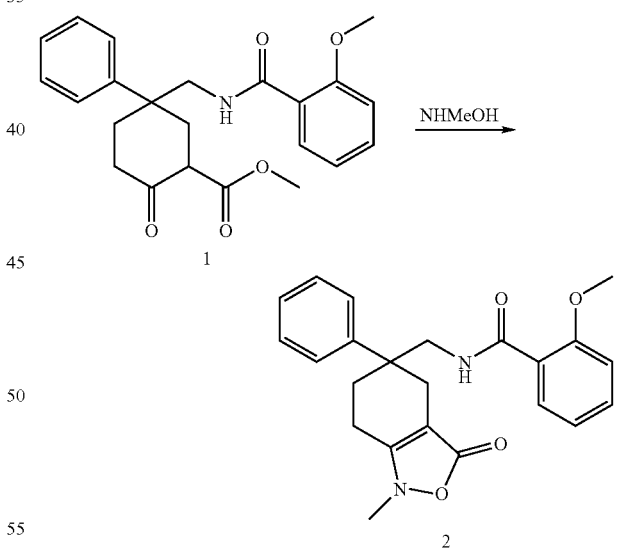

Example 37

2-Methoxy-N-(3-oxo-5-phenyl-1,3,4,5,6,7-hexahydro-benzo[c]isoxazol-5-ylmethyl)-benzamide

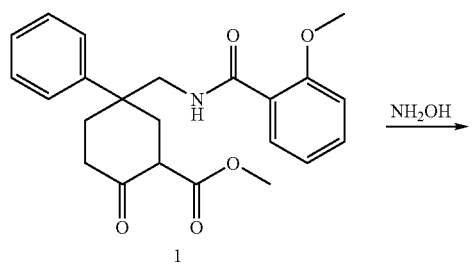

Compound 1: The synthesis of 1 was described in example 36.

Compound 2: To a solution of 1 (17 mg, 0.043 mmol) in EtOH (0.20 mL) was added N-methylhydroxylamine hydrochloride (3.6 mg, 0.043 mmol) and the reaction heated at 80° C. for 9 hours. The reaction was cooled to room temperature, volatiles removed under stream of nitrogen, then the residue was purified on silica gel gradiently eluted with 1 to 3% MeOH/CH₂Cl₂ to give 2 (14 mg, 80% yield) as a clear glass. Rt=1.49 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+]=393.

Example 39

2-Methoxy-N-(6-phenyl-4,5,6,7-tetrahydro-benzo[1,2,3]thiadiazol-6-ylmethyl)-benzamide

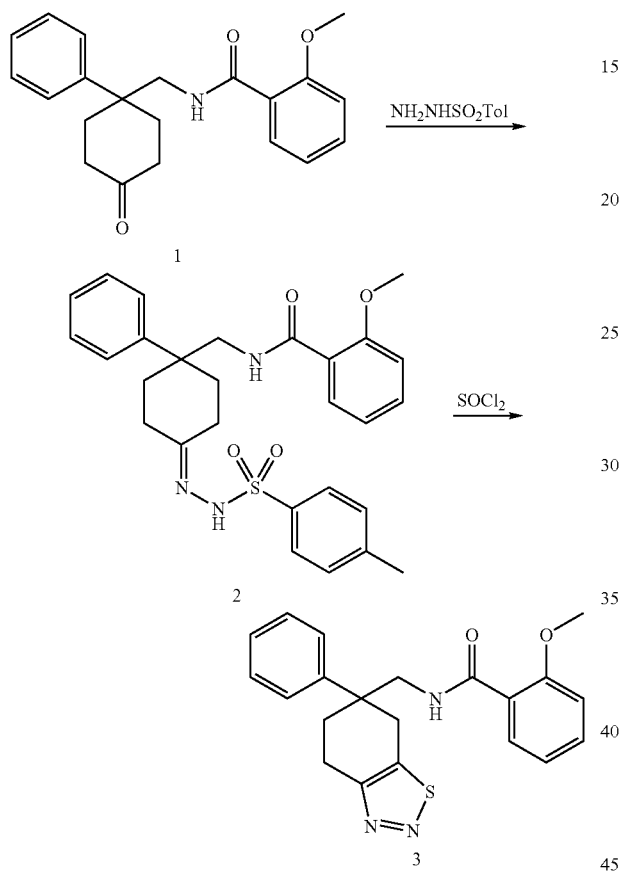

Compound 1: The synthesis of 1 was described in example 1.

Compound 2: To a solution of 1 (75 mg, 0.22 mmol) in MeOH (0.75 mL) was added p-toluenesulfonylhydrazide (41 mg, 0.22 mmol) then the reaction heated at reflux for 4 hours. The reaction was cooled to room temperature then volatiles removed under a stream of nitrogen and the solid place under high vacuum to leave 2 (110 mg, >95% yield) as a white solid. Rt=1.78 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=506

Compound 3: A vial charged with 2 (60 mg, 0.12 mmol) in CH$_2$Cl$_2$ (1 mL) was added thionyl chloride (0.17 mL, 2.4 mmol) and the reaction stirred for 15 hours. Volatiles were removed under a stream of nitrogen and the residue purified by silica gel chromatography, eluted with 50% EtOAc/hexanes, to give 3 (43 mg, 85% yield) as a pale yellow oil. Rt=1.63 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=380.

Example 40

Racemic 2-Methoxy-N-(6-phenyl-4,5,6,7-tetrahydro-1H-indazol-6-ylmethyl)-benzamide

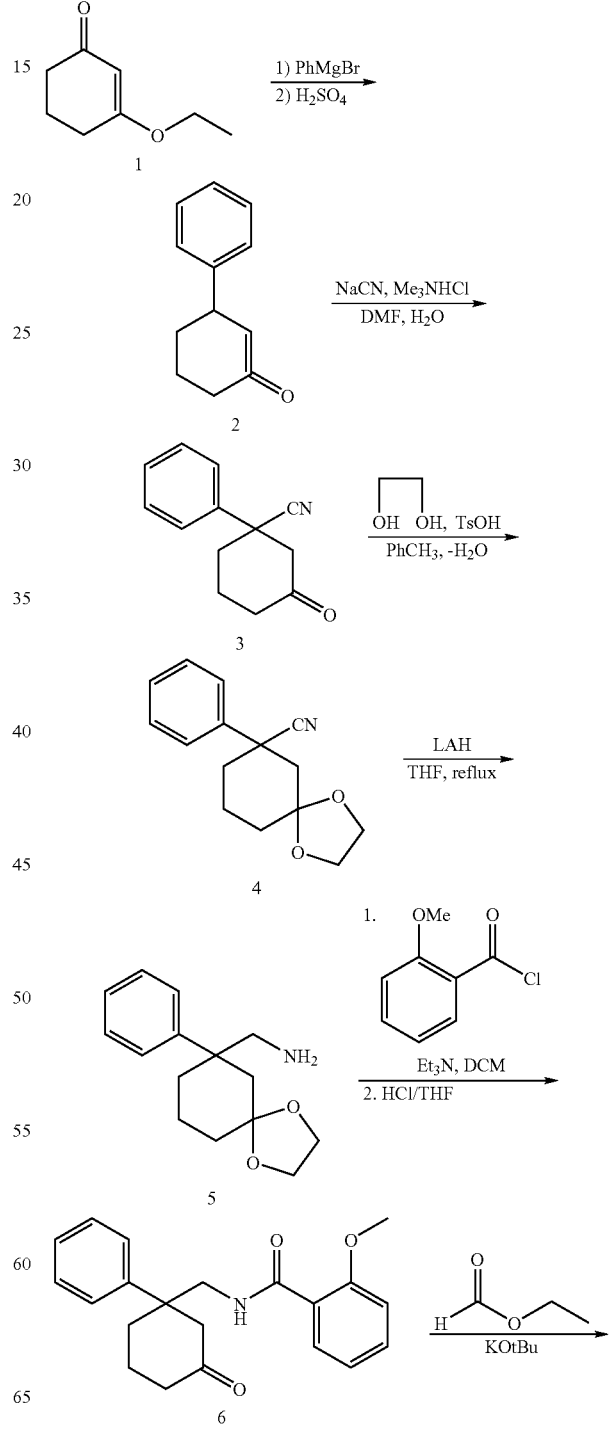

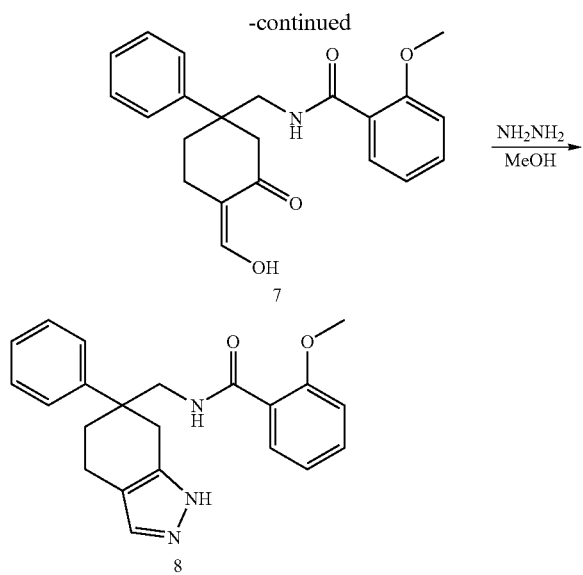

Compound 1: Compound 1 is commercially available from Aldrich. Compound 2: To a solution of phenylmagnesium bromide in THF (1.0 M, 77 mL, 77 mmol) cooled in an ice-bath was added a solution of 3-ethoxy-2-cylohexen-1-one (10 g, 71 mmol) in THF (7 mL) dropwise via cannula. The reaction was stirred at room temperature for one hour then decomposed by the addition of 10% $H_2SO_{4\,(aq)}$ (35 mL) while being cooled. The THF was removed using rotary evaporation, then the residual aqueous solution was diluted with $H_2O$ (50 mL) and extracted with toluene (3×100 mL). The organics were washed with 10% $NaOH_{(aq)}$ (50 mL) and $H_2O$ (50 mL), dried ($MgSO_4$), filtered and solvent removed. The residue was distilled at 138 to 140° C. (1 mm Hg) to give 2 (11.9 g, 98% yield) as a pale yellow oil which solidified upon standing.

Compound 3: To a solution of 2 (5.8 g, 33 mmol) in DMF (110 mL) was added sodium cyanide (3.3 g, 67 mmol) followed by trimethylamine hydrochloride (4.8 g, 50 mmol) and $H_2O$ (20 mL) then the reaction heated at 90° C. for 6 h. Solvents were removed by rotary evaporation then $H_2O$ (50 mL) added to the residue and the aqueous solution extracted with toluene (3×100 mL). The organics were washed with $H_2O$ (50 mL), 10% $HCl_{(aq)}$ (50 mL) and $H_2O$ (50 mL), dried ($MgSO_4$), filtered and solvent removed. The residue was distilled at 148° C. (1 mm Hg) to give 3 (5.2 g, 79% yield) as a viscous pale yellow oil.

Compound 4: To a solution of 3 (2.8 g, 14 mmol) in toluene (40 mL) was added ethylene glycol (8.8 mL, 140 mmol) followed by p-toluenesulfonic acid (150 mg (0.8 mmol) and the reaction heated at reflux with azeotropic removal of water using a Dean-Stark trap for 18 hours. The reaction was cooled to room temperature then poured into satd $Na_2CO_3$ (30 mL) and extracted with $Et_2O$ (3×30 mL), dried ($MgSO_4$), filtered and solvent removed. The residue was purified by silica gel chromatography, eluted with 10 to 20% EtOAc/hexanes to give 4 (3.0 g, 90% yield) as a white solid. $^1H$ NMR ($CDCl_3$, 400 mHz) δ 1.59 (m, 1H), 1.78 (m, 1H), 1.96 (m, 3H), 2.13 (m, 1H), 2.26 (m, 2H), 3.96 (m, 2H), 4.10 (m, 2H), 7.35 (t, 1H, J=8.0 Hz), 7.40 (t, 2H, J=8.0 Hz), 7.51 (d, 2H, J=8.0 Hz).

Compound 5: To a solution of 4 (3.0 g, 12 mmol) in THF (25 mL) was added a 1.0 M solution of LAH in THF (15 mL, 15 mmol) and the reaction was heated at reflux for 2 hours. The reaction was cooled in an ice-bath then slowly quenched by dropwise addition of 4N $NaOH_{(aq)}$ (1 ml), filtered through a pad of $Na_2SO_4$, then volatiles removed to leave the amine 5 (3.0 g, quantitative yield) as a clear oil. The material was used without further purification.

Compound 6: To a solution of 5 (2.0 g 80 mmol) in dichloromethane (35 mL) at ice-bath temperature was added triethylamine (2.0 mL, 14 mmol) followed by o-anisoyl chloride (1.6 mL, 11 mmol) and the reaction stirred for 2 hours. The reaction was diluted with $Et_2O$ (75 mL) then washed with satd $Na_2CO_3$ (25 mL) and solvent evaporated. The residue was brought up into THF (50 mL) then 2N $HCl_{(aq)}$ (17 mL) added and the reaction heated at 40° C. for 3 hours. The reaction was cooled, poured into $Et_2O$ (75 mL) and washed with satd $Na_2CO_3$ (30 mL). The organic layer was dried ($MgSO_4$), filtered and solvent removed and residue was purified by silica gel chromatography, eluted with 10 to 70% EtOAc/hexanes, to give 6 (2.3 g, 83% yield) as a white solid. [M+H]=338.

Compound 7: To a flask charged with 6 (300 mg, 0.90 mmol) was added a 1.0 M solution of potassium tert-butoxide in tert-butanol (3.3 mL, 3.3 mmol) and the reaction stirred for 15 minutes, then ethyl formate (0.26 mL, 3.3 mmol) was added dropwise (gas evolution) and the reaction stirred for 1 hour. The reaction was quenched by the addition of satd $NH_4Cl$ (15 mL) then extracted with $CH_2Cl_2$ (20 ml). The organic layer was washed with brine (10 mL), dried ($Na_2SO_4$), filtered, and concentrated in vacuo to provide 7 as a sticky white solid (320 mg, >95%), which was used in the following reaction without further purification.

Compound 8: To a solution of 7 (95 mg, 0.26 mmol) in MeOH (2 mL) was added hydrazine monohydrate (0.013 mL, 0.26 mmol) and the reaction stirred for 18 hours. Volatiles were removed under a stream of nitrogen then the residue purified by prep HPLC (Rt=17.8 min using Phenomenex Luna 5u C18 30×250 mm column with flow rate of 30 ml/min over 20 min gradient. 20 to 100% Solvent B. Solvent A=10/90/0.1% MeOH/$H_2O$/TFA. Solvent B=90/10/0.1%.) to give 8 (93 mg, 100% yield) as a clear colorless glass. $^1H$ NMR ($CDCl_3$, 400 mHz) δ 2.14 (m, 1H), 2.32 (m, 2H), 2.73 (m, 1H), 3.03 (d, 1H, J=18.0 Hz), 3.49 (d, 1H, J=18.0 Hz), 3.58 (s, 3H), 3.74 (dd, 1H, J=4.8, 13.6 Hz), 3.99 (dd, 1H, J=7.0, 13.6 Hz), 6.87 (d, 1H, 8.4 Hz), 7.04 (t, 1H, 7.5 Hz), 7.29-7.44 (m, 6H), 7.53 (s, 1H), 7.80 (bt, 1H), 8.13 (d, 1H, J=9.2 Hz), 11.0 (bs, 1H).

Example 41

Example 41 was synthesized using methodology described in example 40.

| Ex | Structure | Name | M + H |
|---|---|---|---|
| 41 | 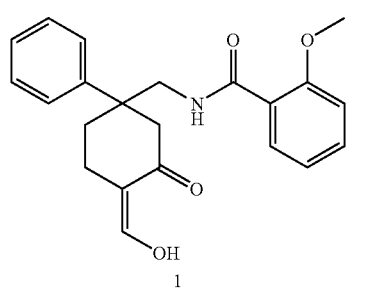 | 2-Methoxy-N-(2-methyl-6-phenyl-4,5,6,7-tetrahydro-2H-indazol-6-ylmethyl)-benzamide | 376 |

Example 42

2-Methoxy-N-(6-phenyl-4,5,6,7-tetrahydro-benzo[d]isoxazol-6-ylmethyl)-benzamide

Example 43

2-Methoxy-N-(6-phenyl-4,5,6,7-tetrahydro-benzo[c]isoxazol-6-ylmethyl)-benzamide

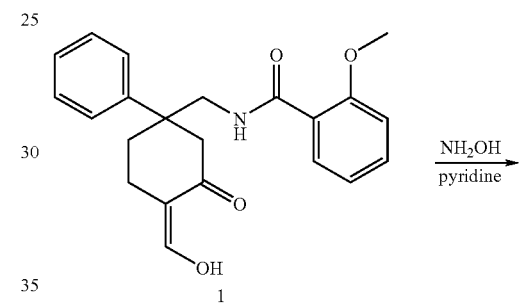

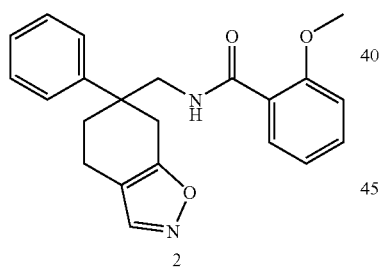

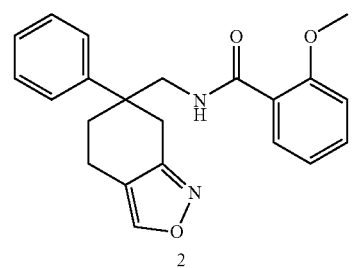 [SMILES: COc1ccccc1C(=O)NCC1(c2ccccc2)CCc2cn[nH]c2C1]

Compound 1: Compound 1 was synthesized as described in example 40.

Compound 2: To a solution of 1 (80 mg, 0.22 mmol) in hot tert-butanol (4 mL) was added hydroxylamine hydrochloride (18 mg, 0.25 mmol) and the reaction heated at reflux for 1.5 hours. The reaction was cooled and volatiles removed on rotary evaporator. The residue was purified by prep HPLC (Rt=7.00 min using YMC S5 ODS 30×100 mm column with flow rate of 40 ml/min over 10 min gradient. 40 to 100% Solvent B. Solvent A=10/90/0.1% MeOH/$H_2O$/TFA. Solvent B=90/10/0.1%.) to give 2 (50 mg, 63% yield) as a clear colorless oil. M+H=363.

Compound 1: Compound 1 was synthesized as described in example 40.

Compound 2: To a solution of 1 (80 mg, 0.22 mmol) in pyridine (4 mL) was added a solution of hydroxylamine hydrochloride (38 mg, 0.55 mmol) in $H_2O$ (0.20 mL) and the reaction heated at reflux for 5 hours. The reaction was cooled and volatiles removed on rotary evaporator. The residue was purified by prep HPLC (Rt=6.57 min using YMC S5 ODS 30×100 mm column with flow rate of 40 ml/min over 10 min gradient. 40 to 100% Solvent B. Solvent A=10/90/0.1% MeOH/$H_2O$/TFA. Solvent B=90/10/0.1%.) to give 2 (49 mg, 61% yield) as a clear colorless oil. M+H=363.

Example 44

2-Methoxy-N-(3-phenyl-2,3,4,9-tetrahydro-1H-carbazol-3-ylmethyl)-benzamide

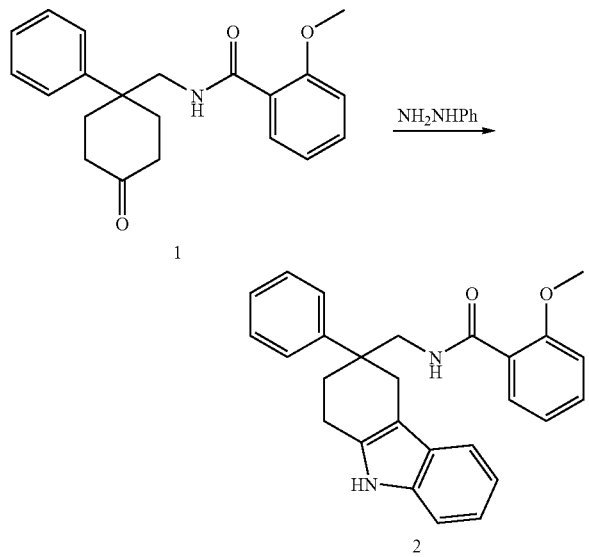

Compound 1: Compound 1 is was synthesized as described in example 1.

Compound 2: To a solution of 1 (90 mg, 0.27 mmol) in acetic acid (2 mL) was added a solution of phenylhydrazine (0.026 mL, 0.27 mmol) in acetic acid (1 mL) and the mixture heated at 50° C. for 1 hour. The reaction was cooled to room temperature then boron trifluoride etherate (0.060 mL, 0.46 mmol) added and the reaction heated at 80° C. for 16 hours. The mixture was diluted with $CH_2Cl_2$ (25 mL) and washed with satd $NaHCO_3$ (3×15 mL, caution: vigorous gas evolution). The organic layer was dried ($Na_2SO_4$), filtered, and concentrated in vacuo. The residue was chromatographed on silica gel, eluted with 40% EtOAc/hexanes, to give 2 (87 mg, 78% yield) as an off-white solid. Rt=1.96 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=411.

Example 45

Example 45 was synthesized using methodology described in example 44.

| Ex | Structure | Name | M + H |
|---|---|---|---|
| 45 | (structure) | 2-Methoxy-N-(9-methyl-3-phenyl-2,3,4,9-tetrahydro-1H-carbazol-3-ylmethyl)-benzamide | 425 |

Examples 46 to 49

2-Methoxy-N-(((6S,7aS)-3-methoxy-6-phenyl-3a,4,5,6,7,7a-hexahydrobenzo[d]isoxazol-6-yl)methyl)benzamide; 2-Methoxy-N-(((3aS,5S)-3-methoxy-5-phenyl-3a,4,5,6,7,7a-hexahydrobenzo[d]isoxazol-5-yl)methyl)benzamide; 2-Methoxy-N-(((3aS,5R)-3-methoxy-5-phenyl-3a,4,5,6,7,7a-hexahydrobenzo[d]isoxazol-5-yl)methyl)benzamide; 2-Methoxy-N-(((6R,7aS)-3-methoxy-6-phenyl-3a,4,5,6,7,7a-hexahydrobenzo[d]isoxazol-6-yl)methyl)benzamide

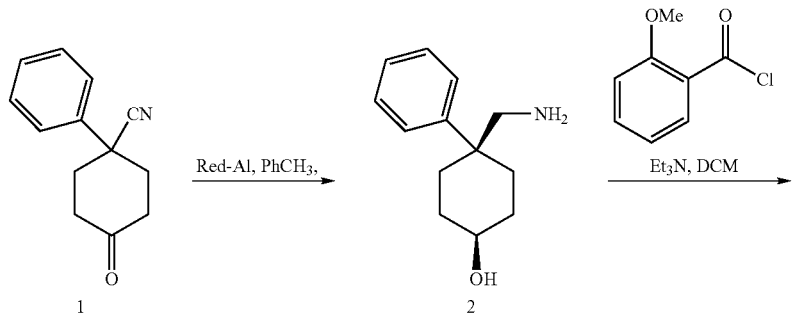

-continued
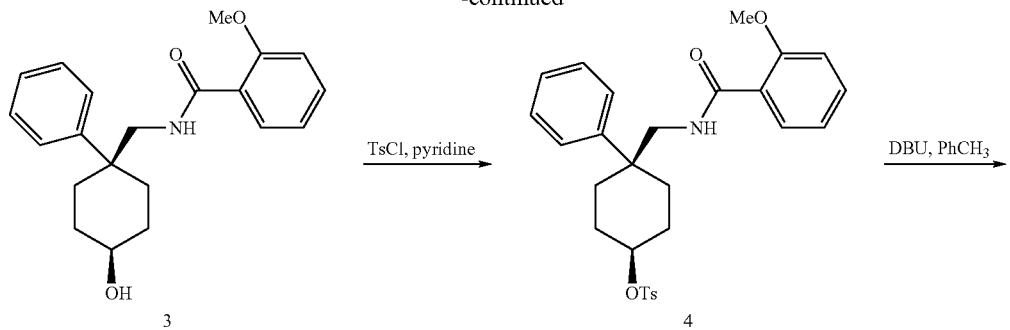
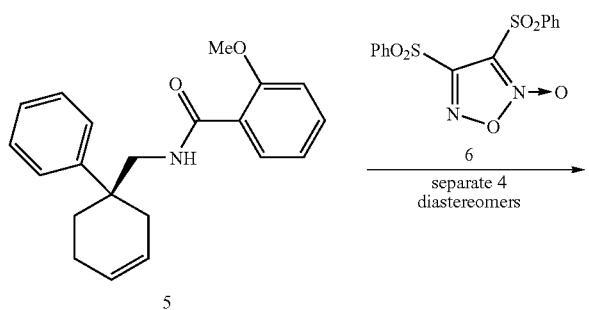
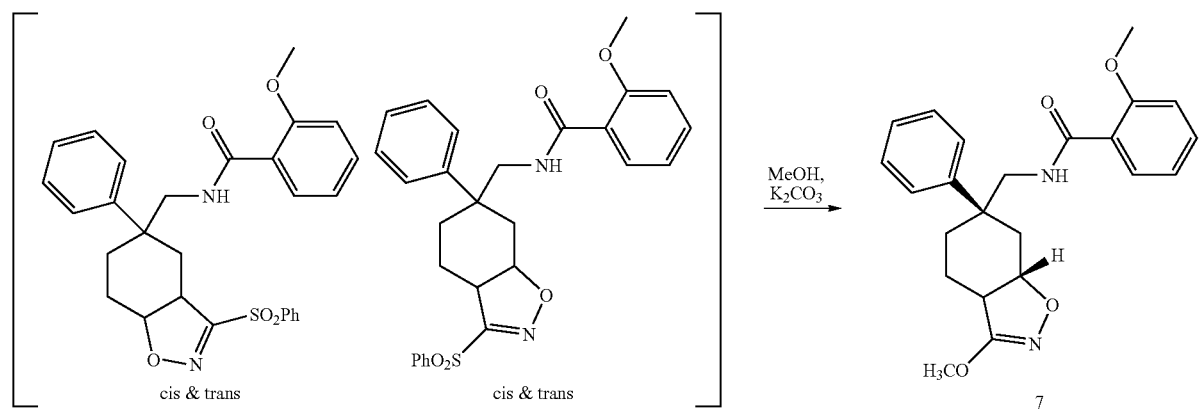
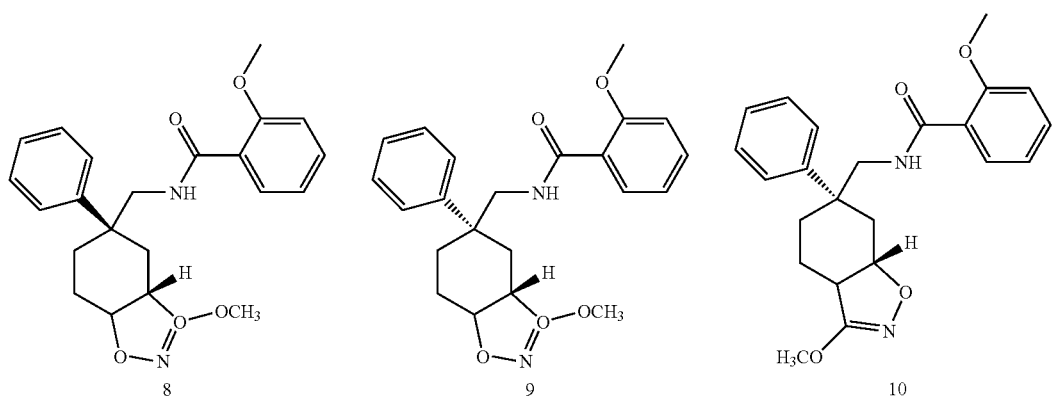

Compound 1: Compound 1 is commercially available.

Compound 2: To a hot solution (110° C.) of Red-Al® (35 mL, 110 mmol) in toluene (150 mL) under a nitrogen atmosphere, solid 4-phenyl-4-cyano-cyclohexane-1-one 1 (10 g, 50 mmol) was added in small portions over 30 minutes. Heating was continued for an additional 30 minutes, the reaction was cooled, excess Red-Al® was decomposed by careful addition of 50% THF-water, and the reaction was digested by portion wise addition of water until a white paste precipitated. The clear supernatant was decanted, the solvent removed under reduced pressure and the residue was flash chromatographed through ammonia treated silica eluting with 25% methanol-methylene chloride providing 2 (8.89 g, 87%) as a yellow solid which was used without further treatment.

Compound 3: To a cold (0° C.) solution of 3 (20.85 g, 102 mmol) in dichloromethane (200 mL) and triethylamine (14.1 mL, 102 mmol) anisoyl chloride was added drop wise and stirred at room temperature for 2 hours. The reaction mixture was washed with two portions of 1 N HCl, dried over magnesium sulfate and the solvent was removed under reduced pressure. The residue was suspended in ethyl acetate, the resulting white solid collected by filtration affording 3 (21.11 g, 51.8%). LC-MS [M+H]=340

Compound 4: To cold suspension (0° C.) of 3 (21 g, 62 mmol) in pyridine (49 mL), toluenesulfonyl chloride (13 g, 68 mmol) was added and the mixture was left to stand for four days. The resulting solid mass was partitioned between methylene chloride and dilute HCl, the organic layer was washed with one portion of dilute HCl, dried over magnesium sulfate, the solvent removed under reduced pressure and the resulting solid was washed by suspension in methanol providing 4 (22.97 g, 75%) as a white powder. LC-MS [M+H]=493.

Compound 5: A mixture of 4 (20 g, 40 mmol) and DBU (18.5 g, 120 mmol) in toluene (300 mL) was heated at reflux for 6 hours, cooled, washed with a saturated aqueous solution of sodium bicarbonate, dried over magnesium sulfate and the solvent was removed under reduced pressure. The residue flash chromatographed eluting with 5% ethyl acetate-methylene chloride afforded 5 (9.82 g, 76%) as a white solid. [M+H]=322

Compound 6: A mixture of phenylsulfonyl acetic acid (12 g, 60 mmol) and nitric acid (18 mL, >90%) in acetic acid (36 mL) was heated at reflux for 1.5 hours, cooled, poured over ice and the solid was collected by filtration. Recrystallization from isopropanol afforded 6 (4.78 g, 44%) as a white solid.

Compounds 7-10: A mixture of 5 (1 g, 3.1 mmol) and 6 (0.8 g, 2.4 mmol} in THF (2 mL) was heated in a microwave reactor (180° C. 10 min.), the solvent, was removed under reduced pressure (LC-MS [M+H]=505) and the isomers were separated by silica gel chromatography (25% ethyl acetate-methylene chloride) without structural assignment. Fraction 1 (311 mg), fraction 2 (318 mg), fraction 3 (168 mg), fraction 4 (222 mg). Each of the individual fractions were dissolved in MeOH (0.2M) and potassium carbonate (6 eq) added then the reaction heated in a microwave reactor (130° C., 10 min.). The potassium carbonate was removed by filtration, the solvent was removed under reduced pressure and the residue was purified by flash chromatography eluting with 10% methanol-methylene chloride affording 7, 8, 9, and 10 (50-80% yield, 2-steps) as white solids. [M+H]=395. Structural assignment was determined by nOE NMR experiments.

Example 50

Racemic N-(2-Amino-6-phenyl-5,6,7,8-tetrahydro-quinazolin-6-ylmethyl)-2-methoxy-benzamide

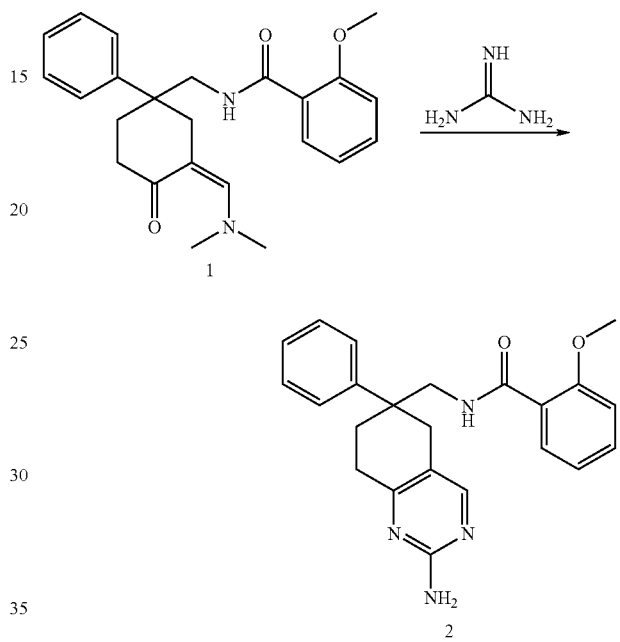

Compound 1: Compound 1 was synthesized as described in example 1.

Compound 2: To a solution of sodium ethoxide (4.3 mg 0.063 mmol) in ethanol (0.5 mL) was added guanidine hydrochloride (6.1 mg, 0.063 mmol) and the mixture stirred for 0.5 hours, then a solution of 1 (25 mg, 0.063 mmol) in ethanol (0.5 mL) was added and the reaction heated at reflux for 3 h. Volatiles were removed under a stream of nitrogen then the residue chromatographed with May 25, 1970 MeOH/hexanes/EtOAc to give 2 (10.3 mg, 42% yield) as a white solid. $^1$H NMR (CDCl$_3$, 500 mHz) δ 2.12 (m, 1H), 2.35 (m, 2H), 2.71 (m, 1H), 2.86 (d, 1H, J=16.8 Hz), 3.21 (d, 1H, J=16.8 Hz), 3.55 (s, 3H), 3.64 (dd, 1H, J=5.0, 13.5 Hz), 3.97 (dd, 1H, J=7.4, 13.4 Hz), 4.84 (s, 2H), 6.84 (d, 1H, J=8.8 Hz), 7.05 (t, 1H, J=7.4 Hz), 7.26 (m, 1H), 7.34 (m, 4H), 7.39 (m, 1H), 7.66 (bt, 1H), 8.08 (s, 1H), 8.19 (dd, 1H, J=1.6, 8.0 Hz). Rt=1.35 min using a Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]= 389.

Examples 51 to 54

Examples 51 to 54 were synthesized using methodology described in example 1.

| Ex | Structure | Name | M + H |
|---|---|---|---|
| 51 | 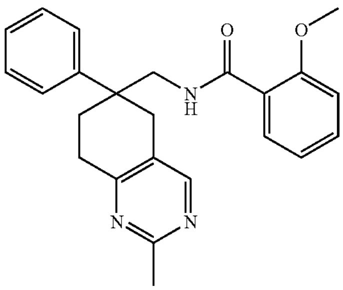 [SMILES: COc1ccccc1C(=O)NCC1(c2ccccc2)CCc2nc(C)ncc2C1] | 2-Methoxy-N-(2-methyl-6-phenyl-5,6,7,8-tetrahydro-quinazolin-6-ylmethyl)-benzamide | 388 |
| 52 | 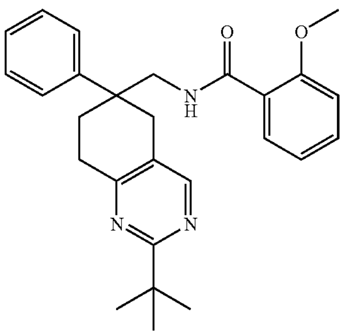 [SMILES: COc1ccccc1C(=O)NCC1(c2ccccc2)CCc2nc(C(C)(C)C)ncc2C1] | N-(2-tert-Butyl-6-phenyl-5,6,7,8-tetrahydro-quinazolin-6-ylmethyl)-2-methoxy-benzamide | 431 |
| 53 | 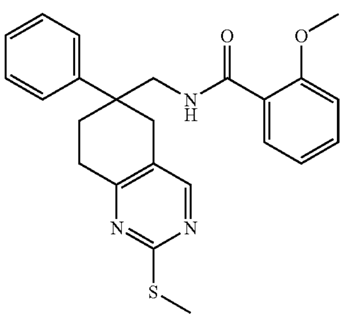 [SMILES: COc1ncc2c(n1)CCC(CNC(=O)c1ccccc1OC)(c1ccccc1)C2] | 2-Methoxy-N-(2-methylsulfanyl-6-phenyl-5,6,7,8-tetrahydro-quinazolin-6-ylmethyl)-benzamide | 421 |
| 54 | 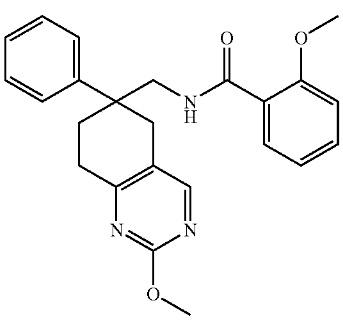 | 2-Methoxy-N-(2-methoxy-6-phenyl-5,6,7,8-tetrahydro-quinazolin-6-ylmethyl)-benzamide | 404 |
| 55 | 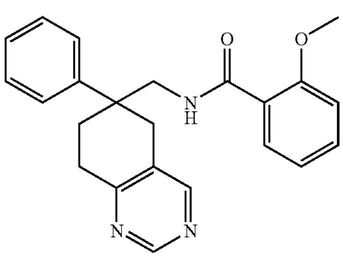 [SMILES: COc1ccccc1C(=O)NCC1(c2ccccc2)CCc2ncncc2C1] | 2-Methoxy-N-(6-phenyl-5,6,7,8-tetrahydro-quinazolin-6-ylmethyl)-benzamide | 374 |

Examples 56 and 57

Enantiomerically Pure N-(2-Dimethylamino-6-phenyl-5,6,7,8-tetrahydro-quinazolin-6-ylmethyl)-2-methoxy-benzamide

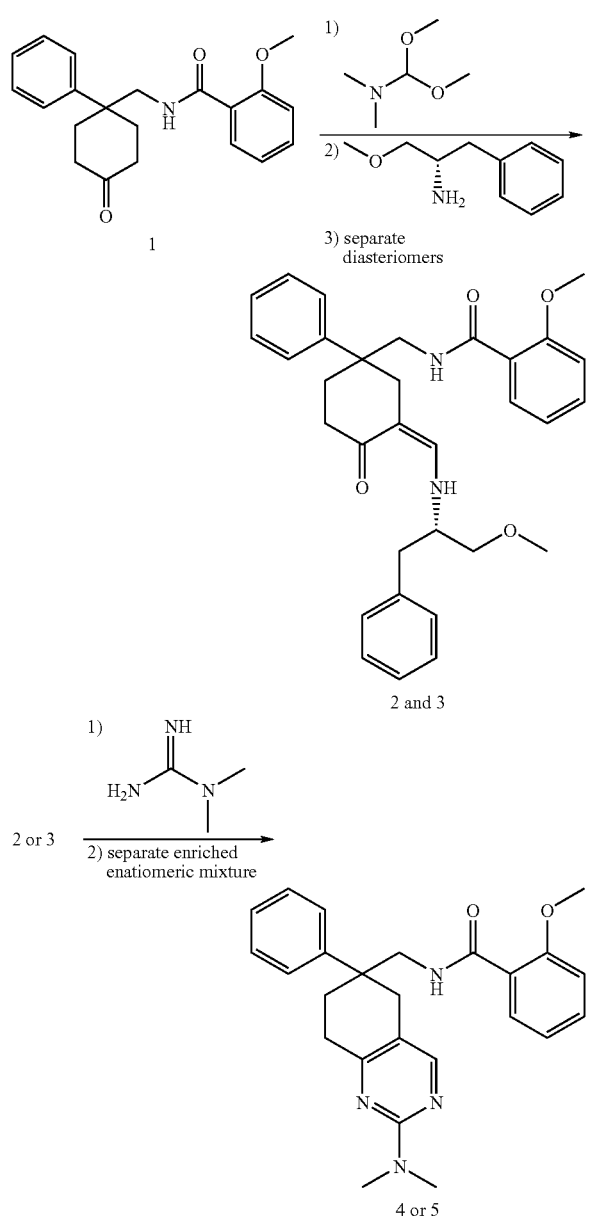

Compound 1: Compound 1 was synthesized as described in example 1.

Compounds 2 and 3: To a suspension of 1 (485 mg, 1.44 mmol) in dimethylformamide (0.20 mL) was added N,N-dimethylformamide dimethylacetal (0.21 mL, 1.58 mmol) and the reaction heated at 110° C. for 24 hours. The solution was cooled to room temperature then diluted ethanol (1 mL). This solution was added to a mixture of (S)-(+)-α-(methoxymethyl)phenethylamine hydrochloride (320 mg, 1.58 mmol) and sodium ethoxide (108 mg, 1.58 mmol), which had been prestirred for 0.5 hours, then the reaction heated at 40° C. for 16 hours. The reaction was cooled to room temperature, volatiles removed under a stream of nitrogen, then the residue chromatographed on silica gel elution with Mar. 47, 1950 MeOH/EtOAc/hexanes to give the less polar diastereomer 2 (132 mg, 18% yield) and more polar diastereomer 3 (207 mg, 28% yield) as white solids. Rt of 2 and 3 was 1.71 and 1.69 min, respectively, using a Phenomenex 30×4.6 5u column with flow rate of 5 mL/min over 2 min gradient. 0 to 100% B. Solvent A=10/90/0.1% MeOH/H2O/TFA. Solvent B=90/10/0.1%.

Compound 4: To a vial charged with 1,1-dimethylguanidine sulfate (33 mg, 0.12 mmol) was added a solution of sodium ethoxide (8.2 mg, 0.12 mmol) in ethanol (0.5 mL) and the mixture stirred for 0.5 hours then a solution of 2 (61 mg, 0.12 mmol) in ethanol (1 mL) added. The vial was sealed then heated in an oil-bath at 100° C. for 40 hours then heated at 190° C. (in microwave) for 1 hour. The reaction was cooled to room temperature, volatiles removed under a stream of nitrogen, and the residue purified by prep TLC, eluted with Feb. 28, 1970 MeOH/EtOAC/hexanes, to give 4 (30 mg, 60% yield) as a white solid. This material was determined to have 93% ee using a DIACEL OD 4.6×250 mm chiral analytical column (Diacel Chemical Industries, Arai Plant, Niigata, Japan, available from Chiral Technologies, Exton, Pa.) (Rt of 11.8 min) with flow rate of 1 mL/min, isocratic elution using 30% isopropyl alcohol/hexanes. This material was purified to 100% ee using a Chiracel OD 5×50 cm 20u chiral preparative column (Diacel Chemical Industries, available from Chiral Technologies, Exton, Pa.), isocratic elution using 30% isopropyl alcohol/hexanes, to give 4 (25 mg, 50% yield) as a white solid. M+H=418.

Compound 5: Compound 5 was synthesized starting from 3 on the same scale and purified in the same manner as 4 to give 5 (30 mg, 0.072 mmol, 60% yield) as a white solid in enantiomerically pure form. Rt of 5 was 10.1 min using a DIACEL OD 4.6×250 mm chiral analytical column with flow rate of 1 mL/min, isocratic elution using 30% isopropyl alcohol/hexanes. M+H=418.

Examples 58 and 59

Enantiomerically Enriched 2-Methoxy-N-(2-methylamino-6-phenyl-5,6,7,8-tetrahydro-quinazolin-6-ylmethyl)-benzamide

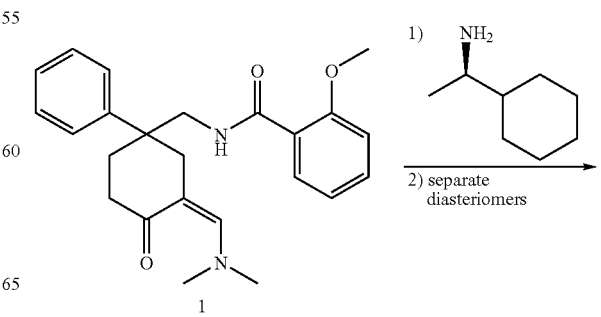

-continued

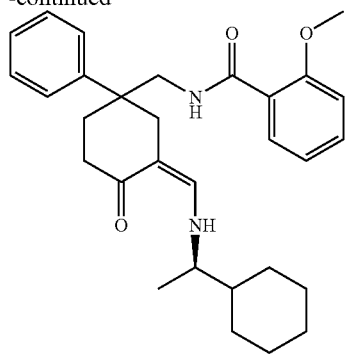

2 and 3

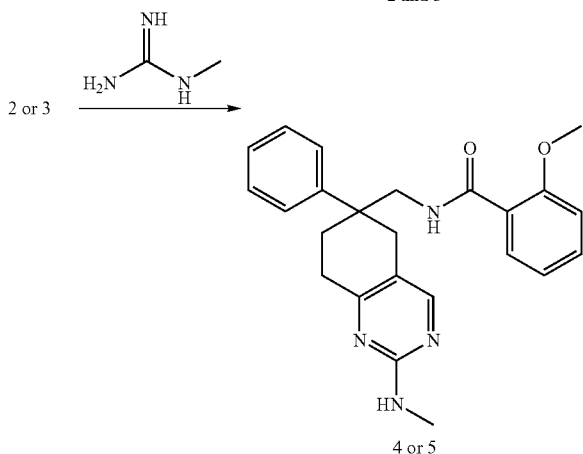

4 or 5

Compound 1: Compound 1 was synthesized as described in example 1.

Compounds 2 and 3: To a solution of 1 (379 mg, 0.97 mmol) in ethanol (1 mL) was added (R)-(−)-1-cyclohexylethylamine (0.16 mL, 1.07 mmol) and the reaction heated at 40° C. for 18 hours. The reaction was cooled to room temperature, volatiles removed under stream of nitrogen, then the residue chromatographed on silica gel eluted with Mar. 40, 1957 MeOH/EtOAc/hexanes to give the less polar diastereomer 2 (116 mg, 25% yield) and more polar diastereomer 3 (117 mg, 25% yield) as yellow oils.

Compound 4: To a solution of 1-methylguanidine hydrochloride (8.2 mg, 0.75 mmol) and sodium ethoxide (4.8 mg, 0.75 mmol) in ethanol (0.75 mL) that had been prestirred for 0.5 hours was added a solution of the less polar diastereomer 2 (22 mg, 0.046 mmol) in ethanol (0.5 mL), then the reaction microwaved at 180° C. for 2 hours. The reaction was cooled to room temperature, volatiles removed, and the residue chromatographed on silica gel eluted with Feb. 30, 1968 MeOH/hexanes/EtOAc to give 4 (6.4 mg, 35% yield) as an off-white solid. The material was determined to have 88% ee using a DIACEL OD 4.6×250 mm chiral analytical column (Rt of 15.4 min) with flow rate of 1 mL/min, isocratic elution using 30% isopropyl alcohol/hexanes. M+H=404.

Compound 5: Compound 5 was synthesized starting from 3 on the same scale and purified in the same manner as 4 to give 5 (6.9 mg, 37% yield) as a white solid. The material was determined to have 83% ee using a DIACEL OD 4.6×250 mm chiral analytical column (Rt of 12.9 min) with flow rate of 1 mL/min, isocratic elution using 30% isopropyl alcohol/hexanes. M+H=404.

Examples 60 to 63

Examples 60 to 63 were synthesized using methodology described in example 7. Compounds synthesized starting from 2 (examples 11 and 13) were generated in 88% ee. Compounds synthesized starting from 3 (examples 12 and 14) were generated in 83% ee.

| Ex | Structure | Name | M + H |
|---|---|---|---|
| 60 | 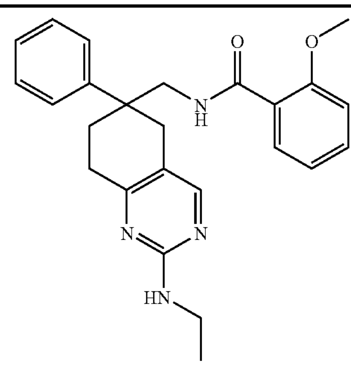 | N-(2-Ethylamino-6-phenyl-5,6,7,8-tetrahydro-quinazolin-6-ylmethyl)-2-methoxy-benzamide | 418 |
| 61 | 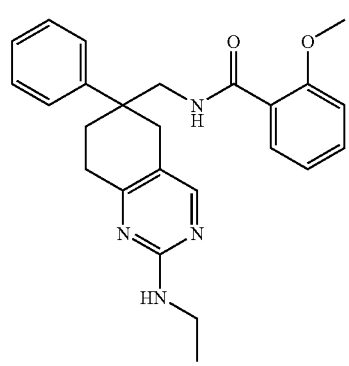 [SMILES: CCNc1ncc2c(n1)CCC(CNC(=O)c1ccccc1OC)(c1ccccc1)C2] | N-(2-Ethylamino-6-phenyl-5,6,7,8-tetrahydro-quinazolin-6-ylmethyl)-2-methoxy-benzamide | 418 |

-continued

| Ex | Structure | Name | M + H |
|---|---|---|---|
| 62 | 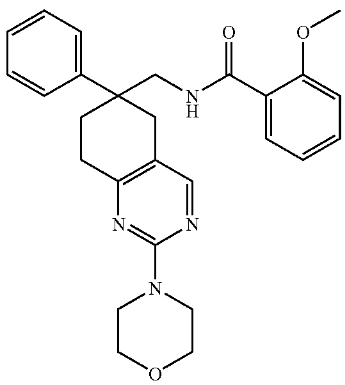 [SMILES: COc1ccccc1C(=O)NCC1(c2ccccc2)CCc2nc(N3CCOCC3)ncc2C1] | 2-Methoxy-N-(2-morpholin-4-yl-6-phenyl-5,6,7,8-tetrahydro-quinazolin-6-ylmethyl)-benzamide | 460 |
| 63 | 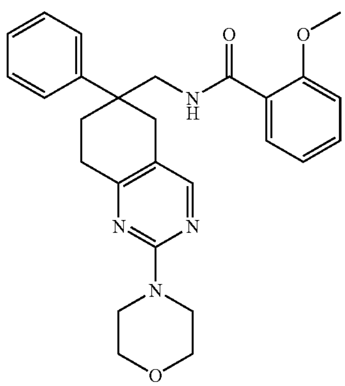 [SMILES: COc1ccccc1C(=O)NCC1(c2ccccc2)CCc2nc(N3CCOCC3)ncc2C1] | 2-Methoxy-N-(2-morpholin-4-yl-6-phenyl-5,6,7,8-tetrahydro-quinazolin-6-ylmethyl)-benzamide | 460 |

Example 64

Racemic N-(2-Dimethylamino-4-methyl-6-phenyl-5,6,7,8-tetrahydro-quinazolin-6-ylmethyl)-2-methoxy-benzamide

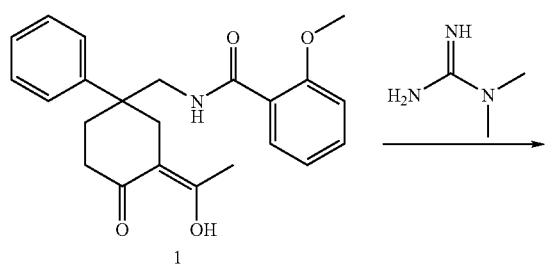

Compound 1: The synthesis of 1 is described in example 33.

Compound 2: To a vial charged with 1 (20 mg, 0.053 mmol), 1,1-dimethylguanidine sulfate (29 mg, 0.11 mmol) and sodium ethoxide (7.2 mg, 0.11 mmol) was added ethanol (0.5 mL). The vial was sealed then placed in an 80° C. oil-bath for 2.5 hours, cooled to room temperature, filtered, then volatiles removed under stream of nitrogen. The residue was purified on silica gel gradiently eluted with 1 to 5% MeOH/$CH_2Cl_2$ to give 2 (13 mg, 58% yield) as a white solid. Rt=1.48 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]= 431.

Example 65

N-(2-Dimethylamino-4-oxo-6-phenyl-3,4,5,6,7,8-hexahydro-quinazolin-6-ylmethyl)-2-methoxy-benzamide

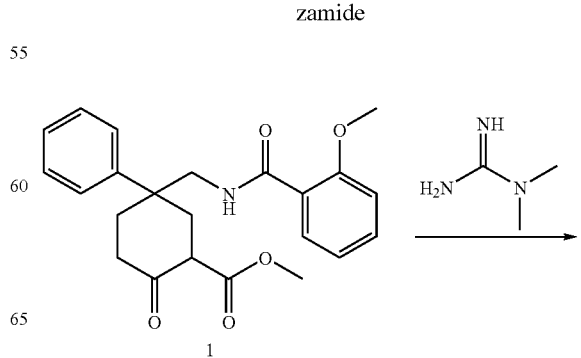

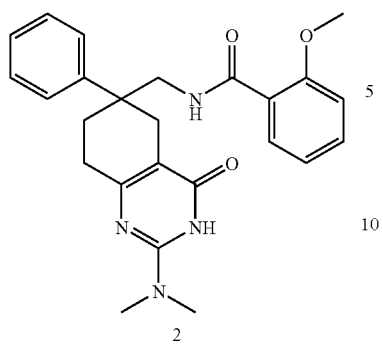

Compound 1: The synthesis of 1 was described in example 36.

Compound 2: To a vial charged with 1 (19 mg, 0.048 mmol), 1,1-dimethylguanidine sulfate (27 mg, 0.10 mmol) and sodium ethoxide (6.8 mg, 0.10 mmol) was added ethanol (1 mL). The vial was sealed then placed in an 80° C. oil-bath for 8 hours, cooled to room temperature, filtered, then volatiles removed under stream of nitrogen. The residue was purified on silica gel gradiently eluted with 1 to 10% MeOH/CH$_2$Cl$_2$ to give 2 (18 mg, 85% yield) as a white solid. Rt=1.33 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=433.

Example 66

Racemic 2-Methoxy-N-(6-phenyl-5,6,7,8-tetrahydro-quinolin-6-ylmethyl)-benzamide

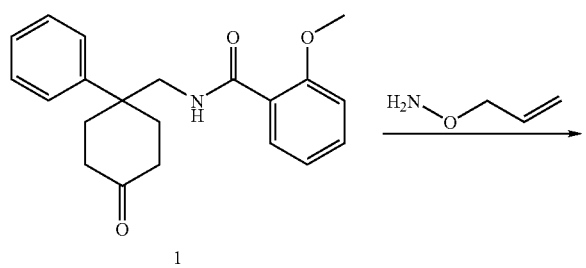

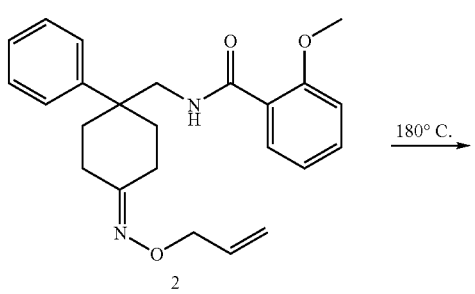

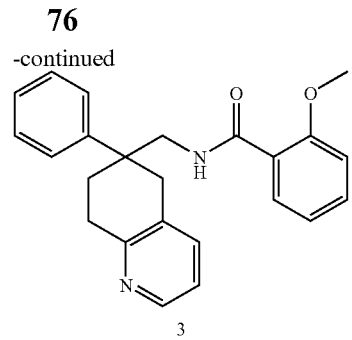

Compound 1: The synthesis of 1 was described in example 1.

Compound 2: To a vial charged with 1 (50 mg, 0.15 mmol) was added sodium acetate trihydrate (52 mg, 0.41 mmol) and o-allylhydroxylamine hydrochloride (26 mg, 0.24 mmol) followed by ethanol (0.5 mL). The vial was sealed an the reaction heated in an 80° C. oil-bath for 2 hours. The reaction was cooled to room temperature, diluted with chloroform (10 mL) and extracted with H$_2$O (3×10 mL). The organic layer was dried (MgSO$_4$), filtered and concentrated in vacuo to give 2 (56 mg, 95% yield) as a white solid. Rt=1.91 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=393.

Compound 3: A vial charged with 2 (30 mg, 0.075 mmol) was sealed under air and heated in an 180° C. oil-bath for 40 hours. The residue was purified on silica gel eluted with 5% MeOH/CH$_2$Cl$_2$ to give 3 (2.6 mg, 10% yield) as a white solid. Rt=1.29 min using Phenomenex 30×4.6 5u column with flow rate of 5 mL/min over 2 min gradient. 0 to 100% B. Solvent A=10/90/0.1% MeOH/H2O/TFA. Solvent B=90/10/0.1%. [M+H]=373.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A compound selected from the group consisting of:
   2-Methoxy-N-(5-phenyl-4,5,6,7-tetrahydro-2H-indazol-5-ylmethyl)-benzamide;
   2-Methoxy-N-(2-methyl-5-phenyl-4,5,6,7-tetrahydro-2H-indazol-5-ylmethyl)-benzamide;
   2-Methoxy-N-(5-phenyl-4,5,6,7-tetrahydro-benzo[d]isoxazol-5-ylmethyl)-benzamide;
   2-Methoxy-N-(5-phenyl-4,5,6,7-tetrahydro-benzo[c]isoxazol-5-ylmethyl)-benzamide;
   N-(1,5-Diphenyl-4,5,6,7-tetrahydro-1H-indazol-5-ylmethyl)-2-methoxy-benzamide;
   N-(2,5-Diphenyl-4,5,6,7-tetrahydro-2H-indazol-5-ylmethyl)-2-methoxy-benzamide;

N-[1-(2-Hydroxy-ethyl)-5-phenyl-4,5,6,7-tetrahydro-1H-indazol-5-ylmethyl]-2-methoxy-benzamide;
N-[2-(2-Hydroxy-ethyl)-5-phenyl-4,5,6,7-tetrahydro-2H-indazol-5-ylmethyl]-2-methoxy-benzamide;
N-[1-(6-Chloro-pyridazin-3-yl)-5-phenyl-4,5,6,7-tetrahydro-1H-indazol-5-ylmethyl]-2-methoxy-benzamide;
N-[2-(6-Chloro-pyridazin-3-yl)-5-phenyl-4,5,6,7-tetrahydro-2H-indazol-5-ylmethyl]-2-methoxy-benzamide;
N-(2-tert-Butyl-5-phenyl-4,5,6,7-tetrahydro-2H-indazol-5-ylmethyl)-2-methoxy-benzamide;
N-(1-Benzyl-5-phenyl-4,5,6,7-tetrahydro-1H-indazol-5-ylmethyl)-2-methoxy-benzamide;
N-(2-Benzyl-5-phenyl-4,5,6,7-tetrahydro-2H-indazol-5-ylmethyl)-2-methoxy-benzamide;
2-Methoxy-N-[5-phenyl-2-(propane-2-sulfonyl)-4,5,6,7-tetrahydro-2H-indazol-5-ylmethyl]-benzamide;
2-Methoxy-N-[5-phenyl-1-(propane-2-sulfonyl)-4,5,6,7-tetrahydro-1H-indazol-5-ylmethyl]-benzamide;
N-(2-Methanesulfonyl-5-phenyl-4,5,6,7-tetrahydro-2H-indazol-5-ylmethyl)-2-methoxy-benzamide;
2-Methoxy-N-[1-(1-methyl-1H-imidazole-4-sulfonyl)-5-phenyl-4,5,6,7-tetrahydro-1H-indazol-5-ylmethyl]-benzamide;
2-Methoxy-N-[2-(1-methyl-1H-imidazole-4-sulfonyl)-5-phenyl-4,5,6,7-tetrahydro-2H-indazol-5-ylmethyl]-benzamide;
2-Methoxy-N-[5-phenyl-2-(2,3,4-trifluoro-benzenesulfonyl)-4,5,6,7-tetrahydro-2H-indazol-5-ylmethyl]-benzamide;
2-Methoxy-N-[5-phenyl-1-(2,3,4-trifluoro-benzenesulfonyl)-4,5,6,7-tetrahydro-1H-indazol-5-ylmethyl]-benzamide;
N-[2-(5-Chloro-1,3-dimethyl-1H-pyrazole-4-sulfonyl)-5-phenyl-4,5,6,7-tetrahydro-2H-indazol-5-ylmethyl]-2-methoxy-benzamide;
N-[1-(5-Chloro-1,3-dimethyl-1H-pyrazole-4-sulfonyl)-5-phenyl-4,5,6,7-tetrahydro-1H-indazol-5-ylmethyl]-2-methoxy-benzamide;
N-[2-(3,5-Dimethyl-isoxazole-4-sulfonyl)-5-phenyl-4,5,6,7-tetrahydro-2H-indazol-5-ylmethyl]-2-methoxy-benzamide;
N-[1-(3,5-Dimethyl-isoxazole-4-sulfonyl)-5-phenyl-4,5,6,7-tetrahydro-1H-indazol-5-ylmethyl]-2-methoxy-benzamide;
2-Methoxy-N-(5-phenyl-4,5,6,7-tetrahydro-1H-benzoimidazol-5-ylmethyl)-benzamide;
N-[1-(3,5-Dimethyl-isoxazole-4-sulfonyl)-5-phenyl-4,5,6,7-tetrahydro-1H-benzoimidazol-5-ylmethyl]-2-methoxy-benzamide;
N-[3-(3,5-Dimethyl-isoxazole-4-sulfonyl)-5-phenyl-4,5,6,7-tetrahydro-3H-benzoimidazol-5-ylmethyl]-2-methoxy-benzamide;
N-[3-(5-Chloro-3-methyl-1H-pyrazole-4-sulfonyl)-5-phenyl-4,5,6,7-tetrahydro-3H-benzoimidazol-5-ylmethyl]-2-ethoxy-benzamide;
N-[1-(5-Chloro-1,3-dimethyl-1H-pyrazole-4-sulfonyl)-5-phenyl-4,5,6,7-tetrahydro-1H-benzoimidazol-5-ylmethyl]-2-methoxy-benzamide;
N-(2-Amino-6-phenyl-4,5,6,7-tetrahydro-benzothiazol-6-ylmethyl)-2-methoxy-benzamide;
N-(2-Acetylamino-6-phenyl-4,5,6,7-tetrahydro-benzothiazol-6-ylmethyl)-2-methoxy-benzamide;
N-(2-Diacetylamino-6-phenyl-4,5,6,7-tetrahydro-benzothiazol-6-ylmethyl)-2-methoxy-benzamide;
2-Methoxy-N-(3-methyl-5-phenyl-4,5,6,7-tetrahydro-1H-indazol-5-ylmethyl)-benzamide;
2-Methoxy-N-(3-methyl-5-phenyl-4,5,6,7-tetrahydro-benzo[d]isoxazol-5-ylmethyl)-benzamide;
2-Methoxy-N-(3-methyl-5-phenyl-4,5,6,7-tetrahydro-benzo[c]isoxazol-5-ylmethyl)-benzamide;
2-Methoxy-N-(3-oxo-5-phenyl-2,3,4,5,6,7-hexahydro-1H-indazol-5-ylmethyl)-benzamide;
2-Methoxy-N-(3-oxo-5-phenyl-1,3,4,5,6,7-hexahydro-benzo[c]isoxazol-5-ylmethyl)-benzamide;
2-Methoxy-N-(1-methyl-3-oxo-5-phenyl-1,3,4,5,6,7-hexahydro-benzo[c]isoxazol-5-ylmethyl)-benzamide;
2-Methoxy-N-(6-phenyl-4,5,6,7-tetrahydro-benzo[1,2,3]thiadiazol-6-ylmethyl)-benzamide;
2-Methoxy-N-(6-phenyl-4,5,6,7-tetrahydro-1H-indazol-6-ylmethyl)-benzamide;
2-Methoxy-N-(2-methyl-6-phenyl-4,5,6,7-tetrahydro-2H-indazol-6-ylmethyl)-benzamide;
2-Methoxy-N-(6-phenyl-4,5,6,7-tetrahydro-benzo[d]isoxazol-6-ylmethyl)-benzamide;
2-Methoxy-N-(6-phenyl-4,5,6,7-tetrahydro-benzo[c]isoxazol-6-ylmethyl)-benzamide;
2-Methoxy-N-(3-phenyl-2,3,4,9-tetrahydro-1H-carbazol-3-ylmethyl)-benzamide;
2-Methoxy-N-(9-methyl-3-phenyl-2,3,4,9-tetrahydro-1H-carbazol-3-ylmethyl)-benzamide;
2-Methoxy-N-(((6S,7aS)-3-methoxy-6-phenyl-3 a,4,5,6,7,7a-hexahydrobenzo[d]isoxazol-6-yl)methyl)benzamide;
2-Methoxy-N-(((3 aS,5 S)-3-methoxy-5-phenyl-3a,4,5,6,7,7a-hexahydrobenzo[d] isoxazol-5-yl)methyl)benzamide;
2-Methoxy-N-(((3 aS,5R)-3-methoxy-5-phenyl-3 a,4,5,6,7,7a-hexahydrobenzo[d]isoxazol-5-yl)methyl)benzamide; and
2-Methoxy-N-(((6R,7aS)-3-methoxy-6-phenyl-3 a,4,5,6,7,7a-hexahydrobenzo[d] isoxazol-6-yl)methyl)benzamide.

2. A compound of claim 1, wherein the compound is 2-Methoxy-N-(6-phenyl-5,6,7,8-tetrahydroquinolin-6-ylmethyl)benzamide.

3. A pharmaceutical composition comprising a therapeutically effective amount of at least one compound of claim 1 and a pharmaceutically acceptable vehicle or carrier thereof.

4. The pharmaceutical composition of claim 3, further comprising at least one other therapeutic agent.

5. The pharmaceutical composition of claim 4, wherein the other therapeutic agent is an anti-arrhythmic agent, a calcium channel blocker, an anti-platelet agent, an anti-hypertensive agent, an anti thrombotic/anti thrombolytic agent, an anti coagulant, an HMG-CoA reductase inhibitor, an anti diabetic agent, a thyroid mimetic, a mineralocorticoid receptor antagonist, or a cardiac glycoside.

* * * * *